United States Patent
Ryu et al.

(10) Patent No.: US 6,717,022 B2
(45) Date of Patent: Apr. 6, 2004

(54) PROCESS FOR SELECTIVE HYDROGENATION OF ALKYNES AND CATALYST THEREFOR

(75) Inventors: J. Yong Ryu, League City, TX (US); Gary R. Gildert, Houston, TX (US)

(73) Assignee: Catalytic Distillation Technologies, Pasadena, TX (US)

( * ) Notice: Subject to any disclaimer, the term of this patent is extended or adjusted under 35 U.S.C. 154(b) by 0 days.

(21) Appl. No.: 10/374,286

(22) Filed: Feb. 25, 2003

(65) Prior Publication Data
US 2003/0171629 A1 Sep. 11, 2003

Related U.S. Application Data

(62) Division of application No. 09/827,411, filed on Apr. 6, 2001, now Pat. No. 6,576,588.
(60) Provisional application No. 60/195,888, filed on Apr. 7, 2000.

(51) Int. Cl.$^7$ .............................. C07C 5/03; C07C 5/05
(52) U.S. Cl. ........................................ 585/261; 585/254
(58) Field of Search ................................. 585/261, 254

(56) References Cited

U.S. PATENT DOCUMENTS

| | | |
|---|---|---|
| 2,620,314 A | 12/1952 | Haskstrin |
| 4,174,355 A | 11/1979 | Patel et al. |
| 4,179,408 A | 12/1979 | Sanchez et al. |
| 4,273,735 A | 6/1981 | Jacques et al. |
| 4,440,956 A | 4/1984 | Couvillion |
| 4,493,906 A | 1/1985 | Couvillion |
| 4,533,779 A | 8/1985 | Boitiaux et al. |
| 4,831,200 A | 5/1989 | Debras et al. |
| 5,028,665 A * | 7/1991 | Hucul ........................ 525/339 |
| 5,110,779 A * | 5/1992 | Hucul ........................ 502/185 |
| 5,134,108 A * | 7/1992 | Thakur et al. ............... 502/318 |
| 5,507,956 A * | 4/1996 | Bonse et al. ................ 210/757 |
| 5,510,568 A | 4/1996 | Hearn |
| 5,595,643 A | 1/1997 | Torimoto et al. |
| 5,597,476 A | 1/1997 | Hearn et al. |
| 5,756,420 A * | 5/1998 | Wittenbrink et al. ....... 502/313 |
| 5,807,477 A | 9/1998 | Hearn et al. |
| 5,877,363 A | 3/1999 | Gildert et al. |
| 5,948,942 A * | 9/1999 | Ramirez de Agudelo et al. ......................... 564/490 |
| 5,977,010 A * | 11/1999 | Roberts et al. ............. 502/244 |
| 6,022,823 A * | 2/2000 | Augustine et al. .......... 502/243 |
| 6,153,556 A * | 11/2000 | Shima et al. ............... 502/348 |
| 6,417,135 B1 * | 7/2002 | Dyroff ........................ 502/325 |

FOREIGN PATENT DOCUMENTS

| | | |
|---|---|---|
| DE | 2109070 | 2/1970 |
| DE | 2412191 | 3/1973 |
| FR | 1253947 | 1/1961 |

* cited by examiner

Primary Examiner—Thuan D Dang
(74) Attorney, Agent, or Firm—Kenneth H. Johnson

(57) ABSTRACT

Acetylenic compounds in olefin streams such as mixed 1,3-butadiene were selectively hydrogenated over the supported copper catalysts on highly porous supports such as alumina, silica, etc. The preferred supports have the average pore diameter larger than about 200 Å, no micro pores, total pore volume larger than about 0.65 cc/g, and preferably less than about 230 m$^2$/g BET surface area. The copper catalysts were preferably promoted with the Group VIII metal such as palladium to improve low activity of copper catalyst. The product stream typically contains less than 20 ppm total alkynes. Also the copper catalysts and the palladium promoted copper catalysts may be modified with zinc oxide to improve the performance of the catalysts. The reactor was loaded with two or more copper catalysts promoted with different levels of palladium. Preferably the copper catalysts were also modified with silver, gold or both silver and gold to reduce polymer formation by the copper component of the catalyst, improve the yield of olefins such as 1,3-butadiene, and prevent the loss of copper and/or palladium due to leaching out into the liquid phase of hydrocarbon.

26 Claims, 15 Drawing Sheets

All reactants enter the catalyst sections in vapor phase only
May have two or more hydrogen feed

PROCESS FOR SELECTIVE HYDROGENATION OF ALKYNES AND CATALYST THEREFOR

This is a division, of application Ser. No. 09/827,411, filed Apr. 6, 2001 now U.S. Pat. No. 6,576,588 which claims the benefit of U.S. Provisional Application No. 60/195,888, filed Apr. 7, 2000.

BACKGROUND OF THE INVENTION

1. Field of the Invention

The present invention relates to the selective removal of more highly unsaturated compounds from mixtures of unsaturated compounds. More particularly the invention is concerned with the selective hydrogenation of acetylenic compounds from mixtures with dienes, such as 1,3-butadiene. The invention provides both novel catalysts and process for the selective hydrogenation of acetylenes in admixture with other unsaturated compounds.

2. Related Information

Supported copper catalysts and palladium catalysts have been preferred catalysts in cleaning up acetylenic impurities in olefin streams by selective hydrogenation. Copper catalysts selectively hydrogenate acetylenic compounds without substantial hydrogenation of the olefins and diolefins (designated herein as selectivity for retaining olefins), but have relatively low activity and short cycle time due to primarily polymer deposition on the catalyst surface. Palladium catalysts have excellent activity and much longer cycle time, but lower selectivity for the acetylenes than copper-based catalysts. To improve olefin selectivity of palladium catalyst, silver or gold has been added to palladium catalyst in minor amounts as modifier.

Fr 1253947 (1960) disclosed the copper catalyst for selective hydrogenation of acetylenic compounds in diolefin or monoolefin streams. The selective hydrogenation was carried out in vapor phase. 99.9–99.999% purity copper was supported on high surface area (25–300 $m^2/g$) supports such as gamma alumina. Copper content of the catalyst was in a range of 5 to 20%. The catalyst may contain less than 0.1% other metals (based on metal content of the catalyst) such as Fe, Ni, Ru, Rh, Pd, Ir or Pt as promoter. The selective hydrogenation was carried out in both vapor and liquid phase. U.S. Pat. Nos. 4,440,956 (1984) and 4,493,906 (1985) disclosed the improved copper catalysts supported on the very specific alumina such as gamma alumina prepared from aluminum alkoxides, which are useful for removing alkynes in liquid hydrocarbon streams. The patentee characterized the gamma alumina as having 60 to 90% of pores which should have a pore diameter between about 40 Å and 120 Å, and not more than 25% nor less than 2% had pore diameter between 1000 Å to 10,000 Å. The nitrogen surface area of the alumina was from about 68 to 350 $m^2/g$ The catalyst contained 3 to 13 weight % Cu. The catalyst contained minor amounts of at least one polyvalent activator metal selected from the group consisting of silver, manganese, cobalt, nickel and chromium. High purity of alumina, especially in terms of sodium (should be less than 0.15 wt %) and $Fe_2O_3$ (less than 0.06 wt %) contents, was claimed to be critical due to shrinkage of the surface area caused by frequent catalyst regeneration.

Ger 2 109 070 (1970) disclosed copper (26%)-zinc oxide catalyst for selective hydrogenation of acetylenic compounds in 1,3-butadiene stream in vapor phase.

U.S. Pat. No. 4,174,355 (1979) disclosed a process for removing (α-acetylenes from diolefin streams by nonselective hydrogenation. The alkynes were removed by contacting the feed steams with CuO and or $Ag_2O$ supported on (α-alumina in the absence of hydrogen or oxygen.

U.S. Pat. No. 4,533,779 (1985) disclosed palladium/gold catalyst supported on supports such as alumina (1 to 100 $m^2/g$) for selective hydrogenation of acetylenic compounds. The contents of palladium and gold in the catalysts were in the range of 0.03 to 1 weight % and 0.003 to 0.3 weight %, respectively.

U.S. Pat. No. 4,831,200 (1989) disclosed the process for the selective hydrogenation of alkynes in olefin streams such as mixtures with 1,3-butadiene. The selective hydrogenation was carried out in two steps in sequence. In the first step, the hydrocarbon feed was passed at least partially in liquid phase with hydrogen over the palladium catalyst such as that disclosed in U.S. Pat. No. 4,533,779 discussed above. In the second step, the product stream from the first step was passed again at least partially in liquid phase with hydrogen over the copper catalyst such as that disclosed U.S. Pat. Nos. 4,493,906 and 4,440,956 discussed above to produce significantly reduced alkyne concentration in the final product stream.

U.S. Pat. No. 5,877,363 (1999) disclosed the process for the selective hydrogenation of acetylenic impurities and 1,2-butadiene in mixed olefin rich $C_4$ streams by using supported hydrogenation catalysts such as Pt and Pd.

In general, the palladium catalysts are very active compared with the copper catalysts for selective hydrogenation of acetylenic compounds in the olefinic steams. But the palladium catalysts exhibit low selectivity for retaining diolefins, such as 1,3-butadiene, when one is trying to remove high concentrations (>2000 ppm) of total alkynes to less than about 500 ppm total alkynes in the streams, especially when the acetylenes are reduced to less than 200 ppm. The non selectivity of palladium catalysts is not desirable in commercial practice, because it resulting in a loss of 1,3-butadiene.

On the other hand, the copper catalysts are highly selective in retaining diolefins such as 1,3-butadiene by being very selective to acetylenes hydrogenation. But the activity of copper catalysts is slow. And the catalyst cycle time is undesirably short for the feed streams, which contain higher than about 2000 ppm total alkynes due to fast deactivation caused by the deposition of polymeric material on the catalyst surface, Even though the hydrogenation is carried out in liquid phase, some of the polymers deposited on the copper catalyst has little solubility in the liquid product stream under the selective hydrogenation condition. Due to these two reasons, the copper catalysts need improvement for the selective hydrogenation of the mixed olefin feeds, which contain relatively high concentration of total alkynes.

SUMMARY OF THE INVENTION

The present invention includes a catalyst comprising a copper component containing from about 0.1 to 25 wt percent Cu, preferably 0.2 to 20 wt %; a palladium promoter in a range of 0 to 2 wt %, preferably 0 to 1 wt %; a silver or gold modifier is in a range of 0 to 15 wt %, preferably 0 to 10 wt %; and a zinc oxide modifier is in a range of 0 to 25 wt %, preferably from 0 to about 15 wt %. The silver modifier moderates the catalyst activity, and improves the olefin yield and the cycle time. The zinc oxide modifier improves the olefin yield such as 1,3-butadiene with small improvement in the catalyst activity. The zinc oxide modified copper catalysts is especially very effective for removing vinyl acetylene impurity with extremely high yield of 1,3-butadiene. In a preferred embodiment the catalyst components are deposited on a support.

The preferred supports have the average pore diameter larger than about 200 Å, no micro pores, total pore volume larger than about 0.65 cc/g, and preferably less than about 230 $m^2$/g BET surface area. The copper catalysts are preferably promoted with the Group VIII metal such as palladium to improve low activity of copper catalyst. The product stream typically contains less than 20 ppm total alkynes. Also the copper catalysts and the palladium promoted copper catalysts may be modified with zinc oxide to improve the performance of the catalysts. The reactor was loaded with two or more copper catalysts promoted with different levels of palladium. Preferably the copper catalysts were also modified with silver, gold or both silver and gold to reduce polymer formation by the copper component of the catalyst, improve the yield of olefins such as 1,3-butadiene, and prevent the loss of copper and palladium due to leaching out into the liquid phase of hydrocarbon.

The process of removing acetylenic compounds by contact hydrocarbon streams containing small amounts of acetylenic compounds with the catalyst of the invention in various arrangements and configurations is also part of the present invention.

DETAILED DESCRIPTION

Figure 1:
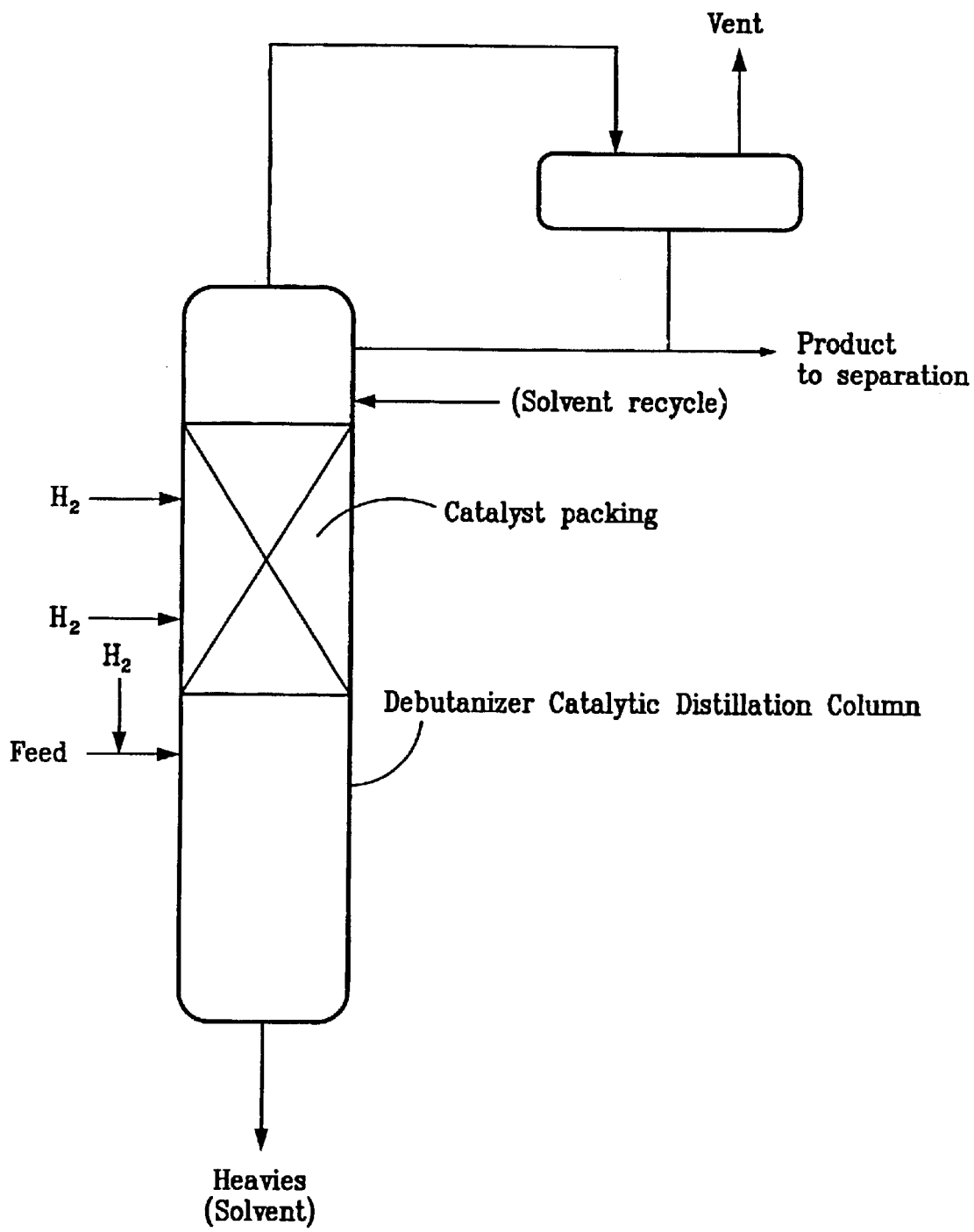
FIG. 1 is a schematic presentation of CD reactor having the present copper catalyst in the upper portion for selective hydrogenation of acetylenes.

The selective hydrogenation is preferably carried out at least partially in liquid phase for example by employing a catalytic distillation (CD) unit(s). Therefore, it is highly desirable to provide a new process and improved copper catalysts so that the selective hydrogenation can be carried out in a single step with higher throughput rate and yet maintaining high selectivity retaining olefins such as dienes and long catalyst life. In this invention, this objective is accomplished by carrying out the selective hydrogenation in a single reactor with the highly active, yet highly selective copper catalysts. The selective hydrogenation is preferably carried out at least partially in liquid phase by employing a catalytic distillation (CD) unit. The distillation column is loaded with two or more copper catalysts promoted with different levels of elements in the Group VIII such as palladium, ruthenium, nickel, etc and also modified with zinc oxide and an element in the Group IB. The preferred promoter is palladium. Promoting copper catalyst with palladium is very desirable in dealing with high acetylenic impurities containing feeds. The present data indicates that copper becomes much more active by alloying with palladium with small loss in the selectivity retaining olefins such as 1,3-butadiene or 1-butene. By alloying copper with palladium, the chemical nature of the copper-palladium catalyst is changed from the traditional palladium or palladium-silver catalysts. The nature of change is demonstrated in the Example 12. The ratio of ethyl acetylene to vinyl acetylene in the product stream from this invention is much higher than the product from the traditional palladium catalysts, because the copper-palladium catalyst has quite different chemical reactivity toward to vinyl acetylene and ethyl acetylene from the traditional palladium or palladium-silver catalyst. Therefore, the difference in the ratios at a given conversion of $C_4$ acetylenes is the fingerprint differentiating the chemical catalytic nature of the copper-palladium catalyst from the traditional palladium catalysts.

The copper catalysts may be loaded in the debutanizer distillation column to provide a CD reactor, in dealing with a mixed $C_4$ feed stream to produce a clean 1,3-butadiene rich product. The feed stream to the catalytic distillation column is preferably fed to the middle section of the column below the catalyst bed. The product is recovered as overhead product. The heavier product is recovered as bottom product. The palladium content of the copper catalysts loaded in the CD reactor gradually decrease as moving up from the bottom section to the top section of the catalyst bed. The catalysts are loaded above the feed point to the distillation column. Hydrogen is fed together with hydrocarbon feed or separately to a position at the bottom section of the distillation column. The optimum ratio of hydrogen to the total alkynes in the catalytic reaction zone depends on the Cu content of the catalyst as wells Cu/Pd weight ratio. Therefore, preferably hydrogen is fed to two or more positions along the catalytic distillation column or the fixed bed depending on the compositions of the catalysts in reactor. Also the palladium component of the catalyst improves the catalyst cycle time. Although it is not known how this additional benefit of the copper catalysts promoted with Pd occur, it may be that unsaturated precursors to polymeric materials are more effectively hydrogenated resulting in slower or little deposition of polymeric material on the copper catalysts. The polymeric materials may have a higher solubility in the product steam than the polymers formed on the unpromoted copper catalysts. Consequently the precursors and polymeric materials are effectively washed off from the catalysts to the bottom of the catalytic distillation column resulting in continuously renewed, cleaner catalyst surface. Preferably the copper component of the catalyst is modified with an element of Group IB such as silver and/or gold or both to reduce further polymer formation to improve the selectivity of diene and improve slowly leaching out the copper and palladium metals from the catalyst.

The catalyst may be modified further with zinc oxide to improve the catalyst activity, the yield of olefins such as 1,3-butadiene, the catalyst cycle time, and reduce the loss of copper and palladium due to slowly leaching out from the catalyst. In the case of the Cu—Zn—Al methanol synthesis catalyst prepared by co-precipitation of mixed solution of nitrate salts, Cu(III) ions dissolves into zinc oxide phase of the copper-zinc oxide-alumina catalyst (prepared by co-precipitation technique) and their concentration could be as high as about 25 at. % (T. M. Yurieva, et al. React. Kinet. Catal. Left., 29, pp. 55–61, 1985). It was observed that all the copper catalysts disclosed in this invention have high content of active hydrogen species that can hydrogenate olefins in the absence of hydrogen regardless of whether or not the catalysts contain zinc oxide.

Figure 2:
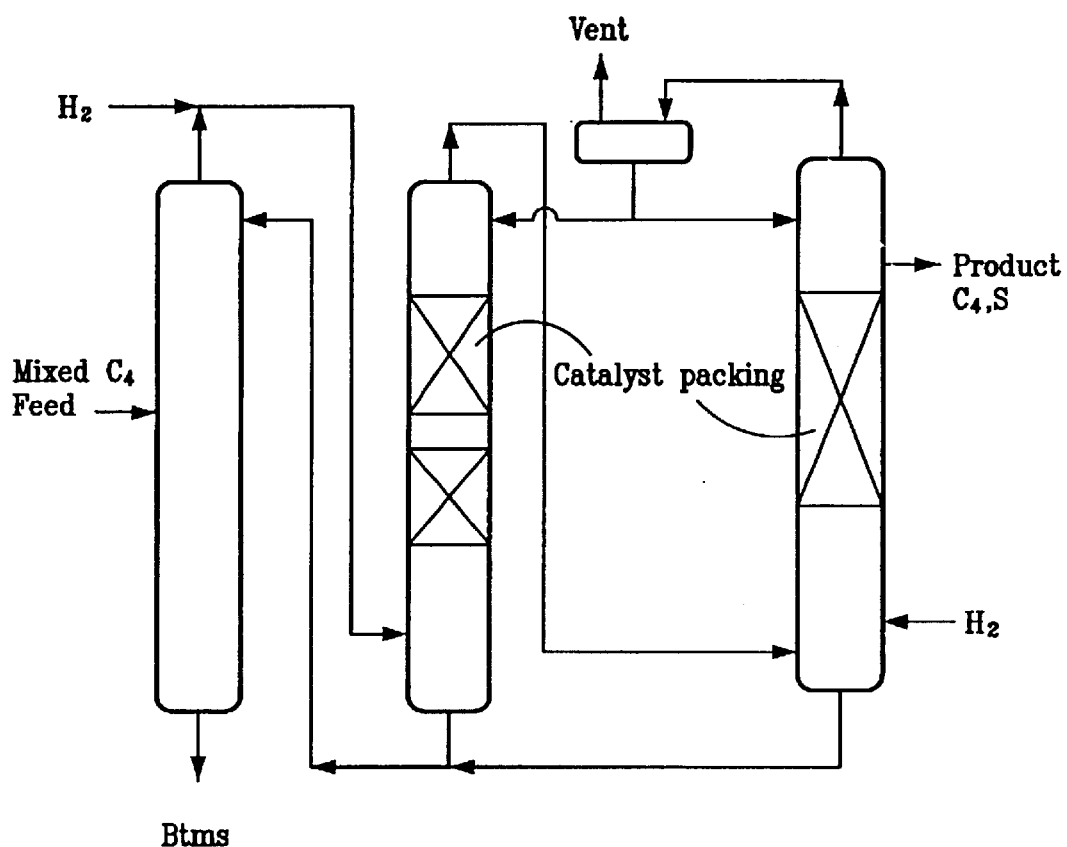
FIG. 2 is a schematic presentation of CD reactor having the present copper catalyst in the upper portion for selective hydrogenation of acetylenes and group VIII catalyst in the lower portion to react mercaptans and diolefins.

The hydrogenation may be carried out in two steps. For example, the selective hydrogenation can be carried out with two CD reactors, or a combination of a CD reactor and a fixed bed reactor, or two fixed bed reactors as shown in FIG. 2. In the fixed bed reactor operation, two or more reactors may be needed, to remove the exothermic heat of the hydrogenation reaction by cooling the reactor effluent stream from the first reactor prior to entering the second reactor. One may recycle the reactor effluent in fixed bed reactor operation to dilute the heat of the hydrogenation reaction. Optionally, material in which the polymer deposited on the catalyst surface is soluble may be used to wash off the polymer from the catalyst in either the reactive distillation mode or the straight pass mode. Examples of such solvents include tetrahydrofuran, furan, 1,4-dioxane, ethers, gamma-butyrolactone, benzene, toluene or mixtures of thereof. After separating products from the solvent, the solvent is recycled back to the reactor as shown in the FIG. 1. Another technique to prolong the catalyst life is washing the catalyst intermittently with a liquid solvent at temperatures in the range of about 40° C. to 350° C. to remove deposited polymers from the catalyst. Optionally a small amount of hydrogen gas is passed through the catalyst bed with solvent during washing off the polymers from the catalyst. When the selective hydrogenation of actelyenes in the $C_4$ streams is carried out in the CD mode, if the boiling point of the solvent is higher than about 100° F., the solvent can be added to the top of the catalyst zone of the catalytic distillation reactor and the solvent flows down to the bottom of the column. In a straight pass reactor the solve may be fed with the reactant feed stream to the reactor. During both modes of operation, it is desirable to apply sufficient pressure so that at least 0.2 mole % of the acetylenes in the feed stream is in the liquid phase which comprises solvent and hydrocarbons in the reaction zone.

The preferred supports to be used for the preparation of the catalyst in this invention are mesoporous materials and should have relatively large pore volume. As the average pore diameter of a supporting material increases, the pore volume increases as well, but both the surface area and ABD (apparent bulk density often called packed density) of the material decrease. Preferably the supports will have no micro pores, preferably no pores less than about 30 Å diameter. When the deposition of heavy material on the catalyst surface causes the catalyst deactivation and deterioration of the selectivity of a desired material due to over-reaction, generally pore size distribution and size of pores play important roles for the catalyst performance. One of preferred supports in this invention is transition alumina. The pores of the desired alumina are mostly composed of pores larger than 100 Å diameter. About 85%, preferably about 90% of pores will have the pore diameter larger than 100 Å determined by nitrogen porosimetry. The preferred alumina will have the average pore diameter larger than about 100 Å, preferably larger than 120 Å, total pore volume larger than about 0.65 cc/g (determined by nitrogen porosimetry), preferably larger than 0.70 cc/g, and preferably the BET surface area of less than about 230 m$^2$/g, most preferably from 30 to 200 m$^2$/g, and the apparent bulk density (ABD) less than about 0.70 g/cm$^3$. The pores of alumina are composed of various size pore diameters. Within a certain range of alumina surface area, the pore distribution of alumina can be manipulated depending on how the aluminas are prepared and calcined. Unlike the alumina disclosed in U.S. Pat. No. 4,440,956, the preferred alumina in this invention will have at least 30%, preferably at least 50% of the pores larger than 100 Å diameter, and a total pore volume larger than about 0.65 cc/g, preferably about 0.75 cc/g.

The preferred alumina disclosed in this invention can be prepared by a number of techniques well known to whom skilled in arts preparing so called active aluminas. One of the preferred aluminas disclosed in this invention can be prepared by so-called oil dropping gelation technique. The examples of the prior arts are disclosed in U.S. Pat. Nos. 2,620,314 (1952), and 4,273,735 (1981). The spherically shaped alumina is prepared from aluminum hydroxychloride sol prepared by digesting aluminum metal in aqueous hydrochloric acid solution. Spherically shaped alumina sol materials, in the form of droplets, are gelled in basic liquid oil phase followed by aging, washing, drying, and calcining to transition state aluminas at various temperatures depending on the desired property of alumina. Alternatively the preferred spherically shaped alumina also can be prepared by oil dropping gelation technique using the dispersed boehmite or pseudoboehmite alumina sols. The example of the prior art is disclosed in U.S. Pat. No. 4,179,408 (1979). The alumina sols are prepared by dispersing suitable boehmite, pseudoboehmite or mixtures of boehmite and pseudoboehmite aluminas in acidic water. The pseudoboehmite or boehmite raw materials are obtained by hydrolyzing aluminum alkoxides and crystallizing or reacting sodium aluminate with aluminum salts such as aluminum sulfate and crystallizing. Various boehmite aluminas or dispersed boehmite aluminas sols are available in market place. Condea is one of the suppliers. To prepare the preferred spherical alumina whose pore structure is disclosed in this invention, Disperal HP 14/2, Dispal 11N7-80, Dispal 23N4-20, Disperal HP 14, Deperal 40, Pural 200, Pural 100, Pural NG, etc. or mixtures of these can be used. Other boehmite aluminas such as Catapal C1, Pural SB, Disperal P2, etc are not preferred raw materials for the preparation of the preferred alumina disclosed in this invention. These materials yield the like aluminas disclosed in the U.S. Pat. Nos. 4,493,906 and 4,440,956.

The preferred alumina in extrudate form can also prepared by extruding the preferred boehmite aluminas discussed above and calcining at elevated temperatures from about 550° C. to 1200° C. Generally transition aluminas are various mixtures of crystalline aluminas such as amorphous, Δ, χ, δ, η, ρ, θ, α, etc and their surface area tends to shrink by repeated exposures to high temperature atmosphere due to slow crystallization to more stable crystal forms. Especially this surface area shrinkage accelerates in the presence of moisture in atmosphere or trace amount of sodium in alumina or both. If gamma alumina is the desired form, the calcination is usually carried out at temperatures from about 550° C. to 700° C.

Unlike the aluminas disclosed in U.S. Pat. Nos. 4,493,906 and 4,440,956, the alumina supports prepared in this oil dropping gelation technique using aluminum hydroxychloride sols contain a very small amount of chlorine. A small amount of sodium or chlorine in alumina disclosed in this invention usually doesn't cause serious problem for the catalytic distillation operation or fixed bed operation with solvent, because of long catalyst cycle time.

The physical shapes of the preferred aluminas in this invention are spheres, extrudates, pellets and granules which have diameter of less than about ¼ inches, preferably ⅛ inches and less than about ½ inches length, preferably less than ¼ inches length for extrudates or pellets.

The copper component of the catalyst is put on the preferred alumina by various impregnation techniques with aqueous solution of cupric salts such as cupric nitrate, cupric acetate, etc. The impregnation product is calcined at from about 100 to 500° C., preferably from 200 to 400° C. to decompose the salts resulting in copper oxide-alumina product. The silver and zinc oxide modifiers are incorporated into the catalyst by co-impregnation of a silver salt such as silver nitrate and a zinc salt such as zinc nitrate with copper salt. Optionally they are incorporated into the copper catalyst by double impregnation. The zinc oxide or both silver and zinc oxide modifiers are put on alumina support prior to impregnating the solution of a copper compound. The impregnation product is calcined at from about 100 to 650° C., preferably from 100 to 600° C. to obtain the copper oxide-silver oxide-alumina catalyst or the copper oxide-silver oxide-zinc oxide-alumina catalyst. Still another technique can be used to prepare the zinc oxide modified copper catalyst by dropping the alumina sols, which contain a desired amount of zinc salt or both zinc and copper salts, into basic oil phase to form gels, followed by aging, washing and calcining at a temperature range of 450° to 1200° C.

The palladium promoter is incorporated into the catalyst by co-impregnating the palladium compound solution such as palladium (II) nitrate, palladium (II) acetate, palladium (II) acetylacetonate, etc. with copper salt solution or a solution containing copper salt and silver salt. Although various impregnation techniques can be used, the preferred impregnation technique of the palladium compound solution or the mixed solutions of palladium compound and copper compound or palladium compound, copper compound and silver compound or palladium compound, copper compound, silver compound and zinc compound is spray coating impregnation by using an atomizer. It is highly desirable to spraying the solutions uniformly on supports. It is also highly desirable to create a fine mist of the palladium solutions using a compressed gas atomizer. When various palladium solutions are spray coated on supports such as alumina, the desired volume of the solution is less than about 90 volume % of the total pore volume (weight of support multiplied by the pore volume per unit weight of support) of the support to be impregnated, preferably less than about 85 volume %.

When highly active copper catalyst promoted with palladium is prepared, the impregnation of catalyst components can be carried out in either a single step or two steps. In the two step impregnation, the impregnation technique, for the first step, alumina support is impregnated with a solution of copper compound or a mixed solution containing copper and zinc compounds or copper, zinc and silver compounds or zinc and silver compounds by using usually incipient pore impregnation technique, followed by drying at a temperature from about 100 to 250° C. and calcination at a temperature from 250 to 700, preferably from 300 to 550° C. In the second step the product from the first step is impregnated with a solution of palladium compound, preferably a mixed solution of palladium and copper compounds or palladium, copper and silver compounds or palladium, copper, zinc and silver compounds or palladium, silver and zinc compounds by using spray coating technique with an atomizer, followed by drying at a temperature from 100 to 250° C. and calcining at a temperature from about 250 to 650° C., preferably from 300 to 550° C.

Another preferred technique incorporating palladium into the copper catalyst is the spray-coating impregnation of a solution of a palladium compound or a mixed solution of a palladium compound such as palladium nitrate and a silver compound such as silver nitrate, while the copper catalyst spheres are rolling down a flat surface tilted at a proper angle, on the copper oxide-alumina catalyst, the copper oxide-alumina, the copper oxide-zinc oxide-alumina catalyst or the copper oxide-silver oxide-zinc oxide alumina catalyst. Relatively high loading (>0.15 wt %) of palladium on the copper catalyst is desired for processing the feeds which contain relatively high content (>~4000 ppm) of total acetylenic compounds. A combination of co-impregnation and the spray-coating impregnation is the most desired technique for high palladium loading on the catalyst. It is very important to produce a fine mist of the palladium solution for the spay-coating impregnation. If the copper catalyst, which is promoted with more than about 0.15% Pd, is desired, a combination of co-impregnation and spray coating impregnation is generally preferred. The impregnation product is calcined in air at from about 100 to 400° C., preferably from 100 to 350° C. to prepare the copper, the copper-silver or the copper-silver-zinc catalysts promoted with palladium.

Optionally the catalysts can be prepared by impregnating mixed solutions of metal salts on the alumina powders which have the physical characteristics of preferred supports described above. The raw materials preparing such alumina powders are suitable boehmite powder and pseudoboehmite powders such as Disperal HP 14/2. The raw materials are calcined at temperatures from about 400° C. to about 750° prior to the impregnation. The impregnation products are calcined at temperature from about 250° to 550° C. in air and shaped to desired size of extrudates or pellets. Optionally the impregnation products are shaped to extrudates or pellets and then the shaped materials are calcined in air at elevated temperature from about 250° C. to 550° C. in air.

The catalyst activation is carried out at from about 60 to 400° C., preferably from 100 to 350° C. in the gas flow containing hydrogen. The content of hydrogen in the gas is gradually increased during the activation from about 5 volume % to 50 volume % or more in the inert gas such as nitrogen. During the catalyst activation, a sufficient amount of gas flow is preferred so that no water vapor condensation on the catalyst would occur. The length of activation depends on the amount of the catalyst in reactor, the hydrogen content in the gas and the activation temperature. In laboratory, from 30 minutes to about 10 hours is sufficient for less than about 100 grams catalyst. In commercial practice, generally much longer activation time would be needed. After the catalyst activation, the residual hydrogen in the reaction zone is flushed out with inert gas. At the start-up of the selective hydrogenation, the content of unsaturated compounds in the feed stream should be kept at very low level in the catalytic reaction zone by using inert diluent such as saturated hydrocarbons until most of hydrogen content in the activated catalyst is consumed. Due to relatively high content of copper on the catalyst, the activated catalyst contains relatively large amount of active hydrogen, which could cause run away temperature in the catalyst bed.

Protecting the selective hydrogenation catalysts such as copper catalysts from poisoning by the sulfur compounds such as alkyl mercaptans is necessary in dealing with real feed streams in commercial practice. To protect the selective hydrogenation catalyst from the poisoning by alkyl mercaptans in feed streams, the sulfur impurities are converted to heavier sulfur compounds by reacting with olefins, acetylenic compounds or dienes over Pd, Ni, etc. catalysts or optionally the catalyst disclosed in this invention, but optimized differently from the selective hydrogenation catalysts to maximize the mercaptan reaction. The heavier sulfur products are removed from light components by simple distillation. It is critically important not to produce $H_2S$ from sulfur compounds during this mercaptan removing operation, because $H_2S$ will poison the selective hydrogenation copper catalysts. In a CD unit, this removal of mercaptans can be carried out concurrently with the selective hydrogenation in a single distillation column. The catalyst for forming higher boiling organic sulfides from mercaptans such as that disclosed in U.S. Pat. Nos. 5,510,568; 5,595,643, 5,597,476 or 5,807,477 is loaded at the bottom of the selective hydrogenation catalyst bed in the CD column. The heavier sulfur compounds is removed as bottom product from the CD column prior to entering to selective hydrogenation reaction zone so that the selective hydrogenation catalysts is protected from the sulfur impurities. It is important to maintain a minimal amount of hydrogen in this mercaptan reaction zone not to produce hydrogen sulfide. If too much hydrogen is available, some of mercaptans may be converted to hydrogen sulfide by hydrodesulfurization of alkyl mercaptans or sulfides. To prevent the formation of hydrogen sulfide, it may be necessary to adjust the hydrogen content in the mercaptan reaction zone differently from that in the catalytic selective hydrogenation reaction zone.

CONTROL EXAMPLE 1

A copper catalyst was prepared according to the Example 1 in U.S. Pat. No. 4,440,956. Gamma alumina (CS 331-1 obtained from UCI, 1/16 inch extrudates and 265 m²/g surface area) was calcined at 700° C. for 3 hours in the ambient atmosphere before use. There was little change in ABD before and after calcination. The calcined alumina had 0.792 g/cc ABD. A solution of 28.7 g $Cu(NO_3)_2 \cdot 2.5H_2O$, $Ni(NO_3)_2 \cdot 6H_2O$, 0.04 g $AgNO_3$, 0.34 g $Cr(NO_3)_3 \cdot 9H_2O$ and 0.34 g $Co(NO_3)_2 \cdot 6H_2O$ in 110 ml deionized water was prepared. 60 g UCI alumina was impregnated with above solution by using a rotary evaporator. After drying the impregnation product in 110° C. in vacuum oven overnight, calcined at 400° C. in a muffle furnace for 3 hours. The ABD of the catalyst was 0.87 g/cc. 22 g of this catalyst was blended with 100 ml 3 mm diameter glass balls and loaded in a vertical stainless reactor (1 inch diameter×20 inch long) used as a conventional reactor. The catalyst was activated by the following procedure; (1) heating the reactor to 230° F. in 100 cc/min $N_2$ gas flow, (2) adding 200 cc/min $H_2$ to the $N_2$ gas flow and then holding for 3 hours at 230° F., (3) shut off $N_2$ gas and increasing $H_2$ gas flow to 300 cc/min, (4) heating the reactor temperature to 662° F. and holding for 3 hours at 662° F. and then cooled the reactor to 147° F. in 30 cc/min $H_2$ gas flow.

A mixed $C_4$ stream composed of 28 wt ppm methyl acetylene, 1034 wt ppm vinyl acetylene and 549 wt ppm ethyl acetylene, 45.23 wt % 1,3-butadiene, 0.10 wt % 1,2-butadiene, 6.05 wt % t-2-butene, 4.22 wt % c-2-butene, 15.36 wt % 1-butene, 18.05 wt % isobutene, 9.34 wt % n-butane, 1.30 wt % isobutane, and 0.19 wt % others was selectively hydrogenated to remove acetylenic impurities at 119 psig pressure. For the first 26 hours on stream time, the feed hydrocarbon and hydrogen rates were 2.2 cc/min (3.6 WHSV) and 31.4 scc/min, respectively. Then the feed rates were changed to 3 cc/min for hydrocarbon (5.0 WHSV) and 27 scc/min for hydrogen rate for the next 24 hours on stream. After that, the feed rates were 2.2 cc/min for hydrocarbon (3.6 WHSV) and 31.4 scc/min for hydrogen rate until the end of the run.

CONTROL EXAMPLE 2

18 grams of the palladium catalyst (0.7% Pd/1.4% Ag on alumina, 2464F obtained from UCI) was mixed with 110 ml 3 mm diameter glass balls and loaded in the same reactor used in the Control Example 1. The catalyst was activated at 180° F. by passing 1 ml/min (measured at ambient temperature) isobutane and 10 cc/min 10 volume % $H_2$ gas in He under 200 psig for an hour. A mixed $C_4$ stream composed of 39 wt ppm methyl acetylene, 5974 wt ppm vinyl acetylene and 1119 wt ppm ethyl acetylene, 46.05 wt % 1,3-butadiene, 0.15 wt % 1,2-butadiene, 5.68 wt % t-2-butene, 3.95 wt % c-2-butene, 14.38 wt % 1-butene, 17.98 wt % isobutene, 9.24 wt % n-butane, 1. 32 wt % isobutane, and 0.54 wt % others was selectively hydrogenated to remove the acetylenic impurities in it. The selective hydrogenation was carried out at the constant temperature 147° F. However, the hydrocarbon and hydrogen feed rates were 3 ml/min (6.1 WHSV) and 36.8 scc/min at the reactor pressure 119 psig, respectively, for the first 79 hours on stream, and then changed to 4.9 ml/min (9.9 WHSV) and 60 scc/min at the reactor pressure 108 psig, respectively.

CONTROL EXAMPLE 3

18 grams of the palladium catalyst (0.2% Pd/0.1% Ag on alumina, CDT-3 obtained from UCI) was mixed with 110 ml 3 mm diameter glass balls and loaded in the same reactor used in the Control Example 1. The catalyst was activated at 180° F. by passing 1 ml/min (measured at ambient temperature) isobutane and 10 cc/min 10 volume % $H_2$ gas in He under 200 psig for an hour.

A mixed $C_4$ stream composed of 39 wt ppm methyl acetylene, 5974 wt ppm vinyl acetylene and 1119 wt ppm ethyl acetylene, 46, 05 wt % 1,3-butadiene, 0.15 wt % 1,2-butadiene, 5.68 wt % t-2-butene, 3.95 wt % c-2-butene, 14.38 wt % 1-butene, 17.98 wt % isobutene, 9.24 wt % n-butane, 1.32 wt % isobutane, and 0.54 wt % others was selectively hydrogenated.

CONTROL EXAMPLE 4

The activated alumina (Alfa 31268, 3.2 mm pellets; 90 m²/g surface area) was ground to 10–20 mesh granules. This granular alumina had about 1 g/cc ABD. A solution of 28.7 g $Cu(NO_3)_2 \cdot 2.5H_2O$, $Ni(NO_3)_2 \cdot 6H_2O$, and 0.04 g $AgNO_3$ in 100 ml deionized water was prepared. 60 g of the granular alumina were impregnated with above solution by using a rotary evaporator. After drying the impregnation product in 110° C. in vacuum oven overnight, calcined at 400° C. in a muffle furnace for 3 hours. 18 g of this catalyst was blended with 110 ml 3 mm diameter glass balls and loaded in the same reactor in the Control Example 1. The catalyst was activated by the following procedure; (1) heating the reactor to 230° F. in 100 cc/min $N_2$ gas flow, (2) adding 200 cc/min $H_2$ to the $N_2$ gas flow and then holding for 3 hours at 230° F., (3) shut off $N_2$ gas and increasing $H_2$ gas flow to 300 cc/min, (4) heating the reactor temperature to 662° F. and holding for 3 hours at 662° F. and then cooled the reactor to 147° F. in 30 cc/min $H_2$ gas flow.

The same feed used in the Control Example 1 was selectively hydrogenated to remove acetylenic impurities at 119 psig pressure. For the first 26.5 hours on stream time, the feed hydrocarbon and hydrogen rates were 1.8 cc/min (3.6 WHSV) and 25.7 scc/min, respectively. Then the feed rates were changed to 2.4 cc/min for hydrocarbon (4.9 WHSV) and 22.1 scc/min for hydrogen rate for the next 24 hours on stream. After that, the feed rates were changed again to 1.8 cc/min for hydrocarbon carbon (3.6 WHSV) and 25.7 scc/min.

EXAMPLE 5

A copper catalyst was prepared according to this invention using the alumina (1/16" diameter spherically shaped) prepared by the oil dropping gelation technique. The physical property of the alumina is summarized in Table 1. The pore size distribution of the alumina is illustrated in FIG. 1. More than about 90% of the pores were larger than 100 Å diameter. The solution of 28.7 g $Cu(NO_3)_2.2.5H_2O$, $Ni(NO_3)_2.6H_2O$, 0.04 g $AgNO_3$, 0.34 g $Cr(NO_3)_3.9H_2O$ and 0.34 g $Co(NO_3)_2.6H_2O$ in 110 ml deionized water was prepared. 60 g alumina was impregnated with above solution by using a rotary evaporator. After drying further the impregnation product in 110° C. in vacuum oven overnight, calcined at 400° C. in a muffle furnace for 3 hours. The physical property of the catalyst is summarized in Table 2. There is only a minor change in the pore structure of the copper catalyst from the alumina support as shown in FIG. 1. 22 g of this catalyst was blended with 100 ml 3 mm diameter glass balls and loaded in the same reactor used in the Control Example 1. The catalyst activation was carried out in the same manner described in the Control Example 1.

The same feed used in the Control Example 1 was selectively hydrogenated to remove acetylenic impurities at 119 psig. For the first 26 hours on stream time, the feed hydrocarbon and hydrogen rates were 2.2 cc/min (3.6 WHSV) and 31.4 scc/min, respectively. Then the feed rates were changed to 3 cc/min for hydrocarbon (5.0 WHSV) and 27 scc/min for hydrogen rate for the next 24 hours on stream time. After that, the feed hydrocarbon and hydrogen rates were 2.2 cc/min (3.6 WHSV), but maintained the hydrogen rate at 27 scc/min until the end of the run.

Figure 3:
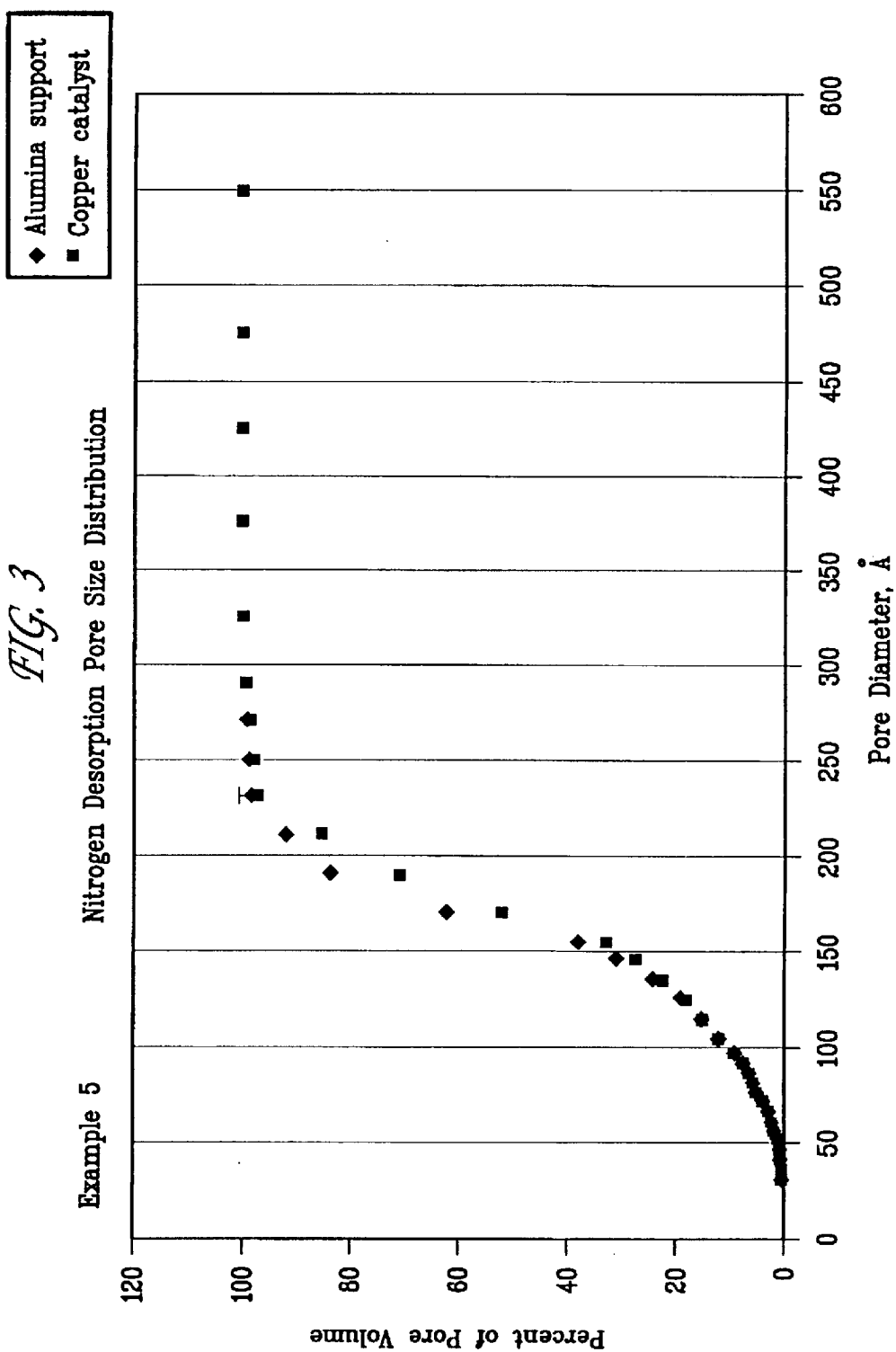
FIG. 3 is a graphic presentation of the pore distribution of alumina support and catalyst of Example 5.
Figure 4:
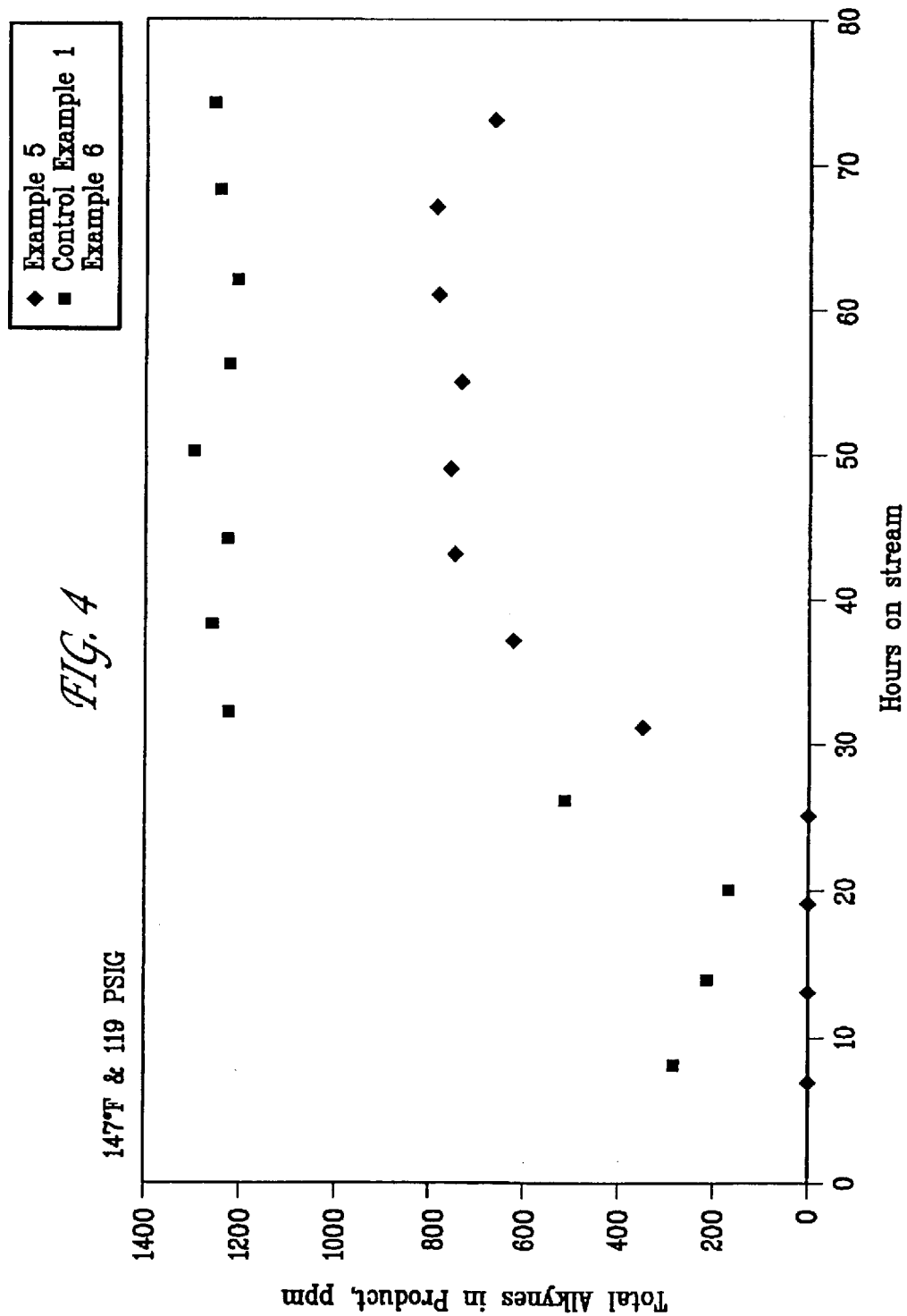
FIG. 4 is a graphic presentation of the total product alkynes in the products of Examples Control 1, 5 and 6.
Figure 5:
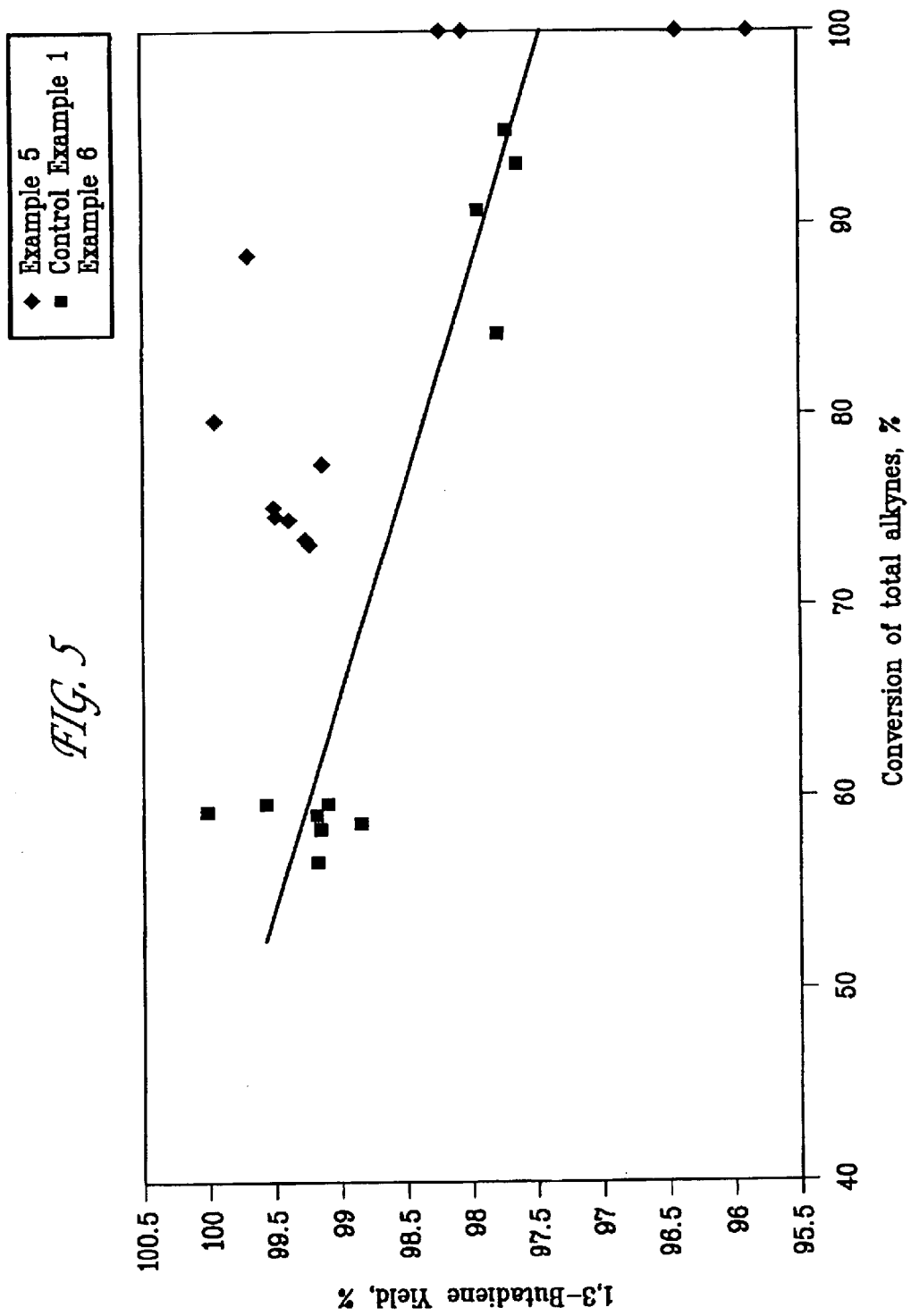
FIG. 5 is a graphic presentation of the total 1,3-butadiene product yield of Examples Control 1, 5 and 6.

The test results of copper catalyst in the Example 5 and the Control Example 1 are illustrated in FIGS. 4 and 5. The FIG. 3 demonstrates the superior catalyst activity and stability of the catalyst disclosed in this invention over the prior art. The FIG. 5 demonstrates a superior butadiene yield of this invention over the prior art. The yields of 1,3-butadiene at the same conversion of the total alkynes over the catalyst disclosed in this invention are higher than those disclosed in the prior art. Also the Example 5 indicates that, if excess hydrogen is available after converting all the acetylenic compounds in the feed stream, the excess hydrogen causes the loss of 1,3-butadiene due to over-hydrogenation, suggesting that the excess hydrogen should be kept to minimal in the selective hydrogenation zone.

TABLE 1

| | |
|---|---|
| ABD, g/cc | 0.53 |
| Single-point BET, $m^2/g$ | 157.5 |
| Multiple-point BET, $m^2/g$ | 170.2 |
| Meso Pore Area, $m^2/g$ | 170.2 |
| Micro Pore Area, $m^2/g$ | 0 |
| Cumulative Adsorption Surface area, $m^2g$ | 172.6 |
| Cumulative Desorption Surface area, $m^2/g$ | 230.4 |
| Total Pore Volume (cc/g) for pores less than 493 Å radius at $P/P_0 = 0.9801$ | 0.912 |
| Cumulative Adsorption Pore Volume for pores (20–300 Å radius) | 0.852 |
| Cumulative Desorption Pore Volume for pores (17.5–300 Å radius) | 0.930 |
| Average Pore diameter, Å | 214.4 |

TABLE 2

| | |
|---|---|
| ABD, g/cc | 0.58 |
| Single-point BET, $m^2/g$ | 137.5 |
| Meso Pore Area, $m^2/g$ | 147.7 |
| Micro Pore Area, $m^2/g$ | 0 |
| Cumulative Desorption Pore Volume for pores (17.5–300 Å radius) | 0.790 |

EXAMPLE 6

The alumina used in the Example 5 was calcined at 700° C. for 3 hours in air. A copper catalyst was prepared using this calcined alumina. The solution of 30 g $Cu(NO_3)_2.2.5H_2O$, $Ni(NO_3)_2.6H_2O$, 0.047 g $AgNO_3$, 0.396 g $Cr(NO_3)_3.9H_2O$ and 0.396 g $Co(NO_3)_2.6H_2O$ in 128 ml deionized water was prepared. 70 g alumina was impregnated with above solution by using a rotary evaporator. After drying further the impregnation product at 110° C. in a vacuum oven overnight, calcined it at 400° C. in a muffle furnace for 3 hours in air. The ABD of the catalyst was 0.57 g/cc. 18 g of this catalyst was blended with 100 ml 3 mm diameter glass balls and loaded in the same reactor in the Control Example. The catalyst was activated in the identical manner as in the Control Example 1.

A mixed $C_4$ stream composed of 444 wt ppm methyl acetylene, 825 wt ppm vinyl acetylene and 634 wt ppm ethyl acetylene, 55.36 wt % 1,3-butadiene, 0.12 wt % 1,2-butadiene, 6.39 wt % t-2-butene, 4.13 wt % c-2-butene, 16.84 wt % 1-butene, 12.38 wt % isobutene, 3.53 wt % n-butane, 0.97 wt % isobutane, and 0.09 wt % others was selectively hydrogenated to remove acetylenic impurities at 119 psig. In this example, the hydrocarbon and hydrogen rates were maintained at constant rates; 3 cc/min for hydrocarbon and 27 scc/min hydrogen. The test results of copper catalyst in the Example 6 and the Control Example 1 are illustrated in FIGS. 4 and 5 along the result from Example 5.

The FIGS. 4 and 5 clearly demonstrate the superior performance of the copper catalysts disclosed in this invention over the prior art.

EXAMPLE 7

In this example, a catalytic distillation column is used for the selective hydrogenation of the acetylenic impurities in a mixed $C_4$ stream. A larger batch catalyst was prepared by using 240 grams of alumina in the exactly same manner described in the Example 5. The catalyst (99.88 grams) was loaded in a catalytic distillation column (1" diameter×25' height). The height of the catalyst bed in the column was 6 feet. 80 inches of top and bottom of the catalyst bed was packed with ¼" saddles. The catalyst was activated in the same manner described in the Control Example 1 except that the flow rate of gases were increased proportionally based on the catalyst weight.

Figure 6:
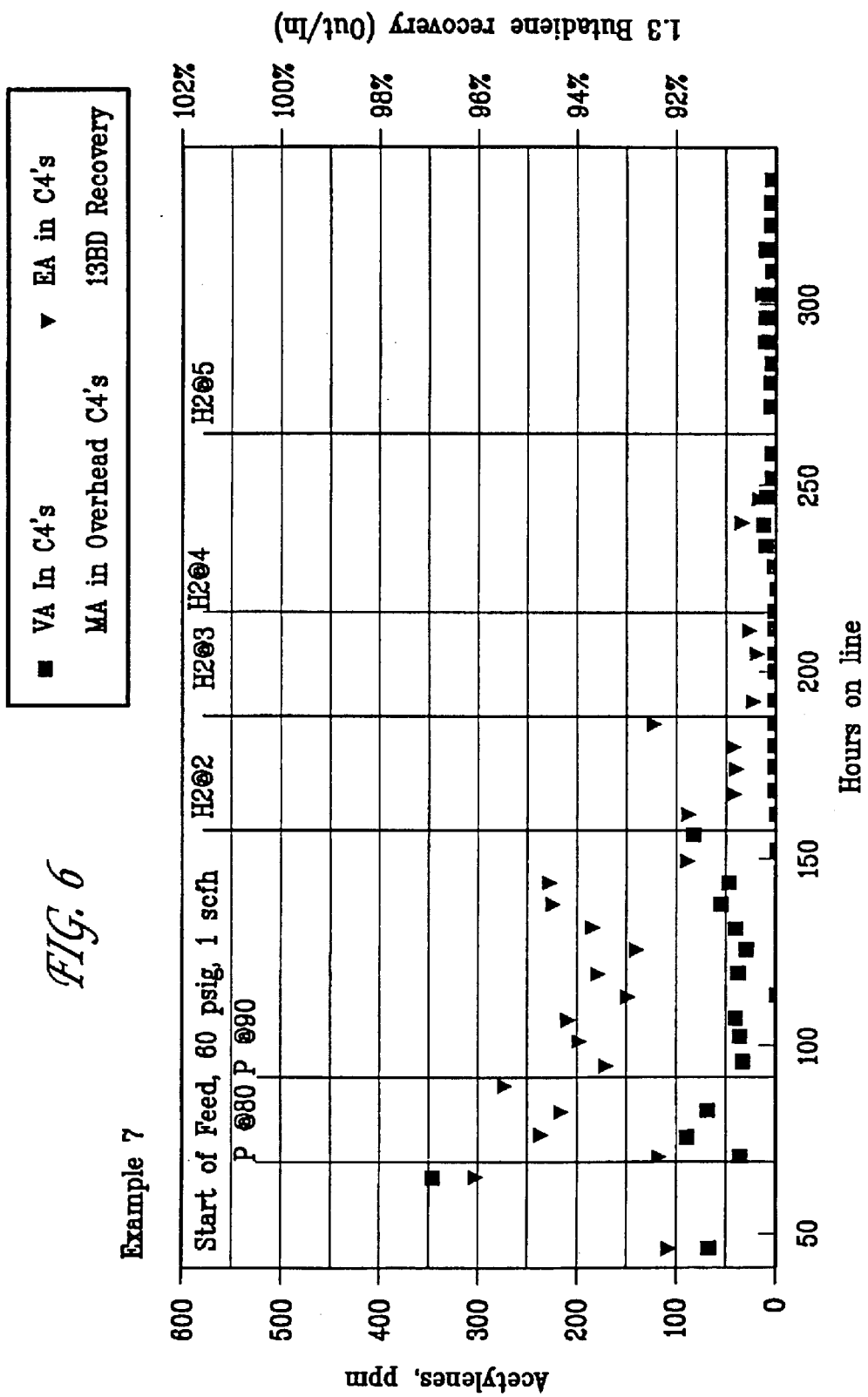
FIG. 6 is a graphic presentation of the results of Example 7 in CD.

The acetylenic impurities in the same feed used in the Example 6 were removed by carrying out the selectively hydrogenation in the catalytic distillation mode. The hydrocarbon feed rate was 1.2 pounds per hour. The hydrogen rate was 1 scf per hour at the beginning of the run, but during the run it was changed to higher rates. The hydrocarbon and hydrogen feeds were fed at point of below the saddle packing. The result is illustrated in FIG. 6. At the hydrogen rate of 3 scf per hour or higher, ethyl acetylene and vinyl acetylene in the feed were practically all removed. Near complete recovery of 1,3-butadiene was obtained. As shown in FIG. 6, the catalyst was much more stable under the catalytic operation mode than the fixed bed operation.

EXAMPLE 8

This experiment was carried out to demonstrate the beneficial effect of zinc oxide incorporation into the copper catalyst disclosed in this invention to improve the performance of the copper catalyst. A copper catalyst was prepared according to the identical procedure used in the Example 5.

Example 5 was loaded in the same reactor used in the Control Example 1. The mixed $C_4$ feed used in this example had the following composition; 20 ppm methyl acetylene, 588 ppm vinyl acetylene, 599 ppm ethyl acetylene, 44.51 wt % 1,3-butadiene, 0.07 wt % 1,2-butadiene, 6.29 wt % t-2-butene, 4.33 wt % c-2-butene, 15.97 wt % 1-butene, 18.04 wt % isobutene, 9.36 wt % n-butane, 1.30 wt % isobutane, and 0.01 wt % others. After on 176 hours on stream time, the catalyst was washed to remove the polymers deposited on the catalyst with THF after flushing out the reactor with $N_2$ gas; 10 cc/min THF, 66.9 scc/min $H_2$ at 147° F. and 200 psig for 1 hour and then at 157° F. for 5 hours. After flushing out the reactor with $N_2$ gas, the selective hydrogen was continued. The constant temperature (147° F.) and pressure (119 psig) were maintained during the run. The run conditions during this experiment are listed in Table 3.

Figure 9:
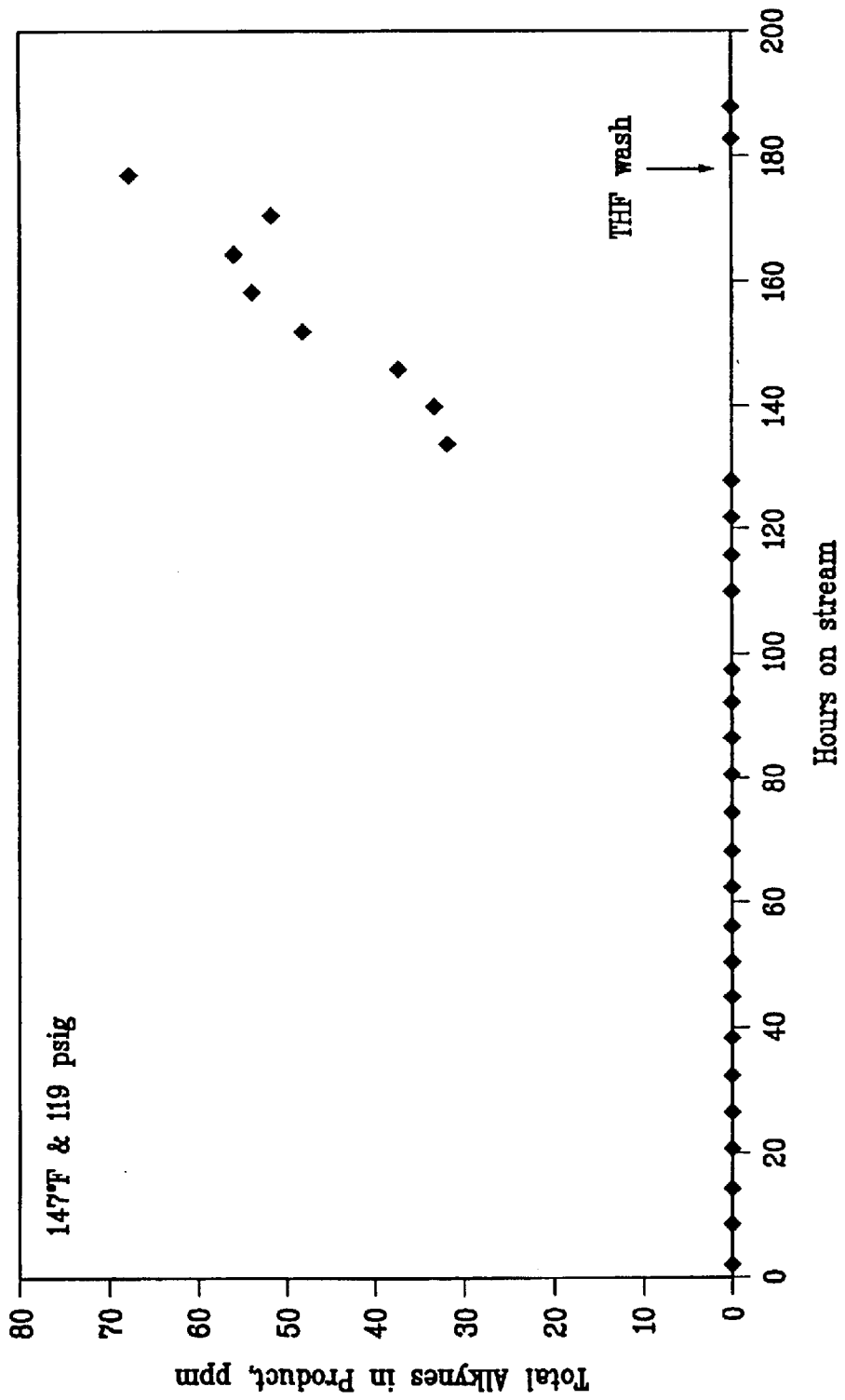
FIG. 9 is a graphic presentation of the benefit of solvent treatment of the used catalyst.

The result of this experiment is illustrated in FIG. 9. The break through of the acetylenic impurities occurred on 128 hours on stream as shown in FIG. 9. But after washing the catalyst with THF, the product obtained under the same condition for the break-through contained no detectable amount of acetylenic impurities. Therefore, THF

TABLE 3

147° F. and 119 psig

| Hours on stream | 0–26 | 26–50 | 50–74 | 74–98 | 98–128 | 128–152 | 152–176 | THF wash | 176–188.5 |
|---|---|---|---|---|---|---|---|---|---|
| HC Feed rate, ml/min | 2.9 | 5.8 | 2.9 | 2.9 | 5.8 | 7 | 7 | wash | 7 |
| $H_2$ rate, scc/min | 45 | 45 | 45 | 15 | 10 | 45 | 45 | 54. | 45 |
| | | | | | Break through of acetylenes | | | | |

The mixed solution of 22.6 g $Cu(NO_3)_2.2.5H_2O$, $Ni(NO_3)_2.6H_2O$, 0.04 g $AgNO_3$, and 4.0 g $Zn$ $(NO_3)_2.6H_2O$ in 100 ml deionized water was prepared. 60 g of the same alumina used in the Example 5 was impregnated with above solution by using a rotary evaporator. After drying further the impregnation product in 110° C. in vacuum oven overnight, calcined at 400° C. in a muffle furnace for 3 hours. 18 g of this catalyst was blended with 100 ml 3 mm diameter glass balls and loaded in the same reactor used in the Control Example 1. The catalyst activation was carried out in the same manner described in the Control Example 1.

Figure 7:
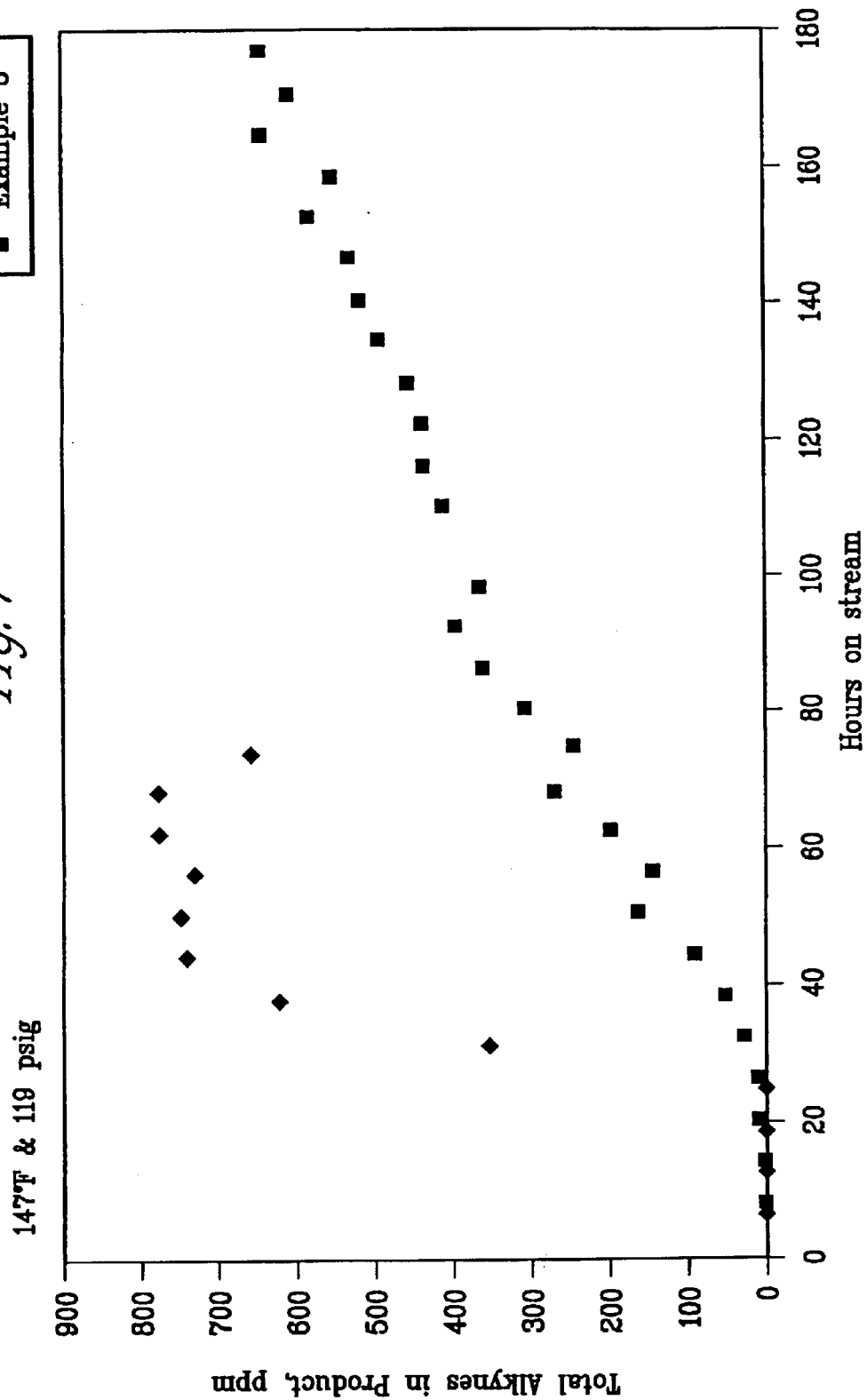
FIG. 7 is a graphic presentation of total alkynes in the products of Example 5 (non CD) and Example 8 (CD).

A mixed $C_4$ stream composed of 475 ppm methyl acetylene, 959 wt ppm vinyl acetylene and 731 wt ppm ethyl acetylene, 54.87 wt % 1,3-butadiene, 0.12 wt % 1,2-butadiene, 6.42 wt % t-2-butene, 4.16 wt % c-2-butene, 16.76 wt % 1-butene, 12.53 wt % isobutene, 3.56 wt % n-butane, 1.27 wt % isobutane, and 0.09 wt % others was selectively hydrogenated to remove the acetylenic impurities in it. The selective hydrogenation was carried out at the constant temperature 147° F. and 119 psig. The constant hydrocarbon and hydrogen feed rates were used throughout the run; 3 ml/min (6.1 WHSV) and 27.1 scc/min. The result of this run is summarized in FIGS. 7 and 8. The beneficial effects of the zinc oxide incorporated into the copper catalyst on the catalyst performance are clearly demonstrated in this example.

EXAMPLE 9

In this example, the usefulness of one of the preferred solvents disclosed in this invention, tetrahydrofuran (THF), is demonstrated. The copper catalyst (36 grams) prepared in is one of the preferred solvents for the catalyst regeneration. Also THF is one of the preferred solvents to be used for carrying out the selective hydrogenation using catalytic distillation column. When THF is used as the solvent in CD selective hydrogenation, THF can be fed to the distillation column above the catalyst bed or it can be feed to the column with the mixed $C_4$ feed stream. The different conditions for the column operation will be needed for these two cases. In the latter case, the column will be operated under the total internal reflux condition with respect to THF. THF will be removed from the column as the bottom product for both cases and recycled to the column. However, a part of the recycle THF stream will be purified in a separator to avoid the heavies build-up in the recycle stream before returning to the column.

EXAMPLE 10A

The copper catalyst prepared in the Example 5 was tested for the selective hydrogenation of the acetylenic impurities (7132 ppm total acetylenes) in the mixed $C_4$ feed used in the Control Example 2.18 g of the catalyst was blended with 100 ml 3 mm diameter glass balls and loaded in the same reactor in the Control Example 1. The catalyst was activated in the identical manner as in the Control Example 1.

The selective hydrogenation was carried out at a constant temperature 147° F. and 119 psig. The hydrocarbon and hydrogen feed rates were 2.9 ml/min (5.87 WHSV) and 45 scc/min, respectively, for the first 66.5 hours on stream, and then changed to 1.4 ml/min (2.83 WHSV) and 24.1 scc/min, respectively.

EXAMPLE 10B

A copper catalyst promoted with palladium was prepared according this invention. The alumina used in the Example 5 was calcined at 900° C. for 3 hours in air. A mixed solution was prepared by dissolving 28.7 g $Cu(NO_3)_2.2.5H_2O$, $Ni(NO_3)_2.6H_2O$, 0.04 g $AgNO_3$, 0.34 g $Cr(NO_3)_3.9H_2O$ and 0.34 g $Co(NO_3)_2.6H_2O$ in 110 ml deionized water. The above calcined alumina (60 g) was impregnated with this solution by using a rotary evaporator. After further drying the impregnation product at 110° in a vacuum oven overnight, it was calcined at 400° C. in a muffle furnace for 3 hours in air. 5.469 grams of aqueous palladium(II) nitrate solution (Aldrich 38,004-0; 10 wt % $Pd(NO_3)_2$ in 10 wt % nitric acid) was sprayed on the copper catalyst spheres (29.762 grams) by using an atomizer, while the copper catalyst spheres were rolling around on the flat surface, to evenly coat the spheres with the palladium solution. It is very important to produce a fine mist of the palladium salt solution. The palladium solution sprayed product was calcined at 250° C. for 2 hours in air. The ABD of the Cu/Pd catalyst was 0.52 g/cc. The analysis of this catalyst indicates 8.20% Cu, 0.71% Pd, 0.20% Ni, 0.11% Cr, and 0.17% Ag.

22 g of this catalyst was blended with 100 ml 3 mm diameter glass balls and loaded in the same reactor used in the Control Example 1. The catalyst was activated by the following procedure; (1) heating the reactor to 230° F. in 100 cc/min $N_2$ gas flow, (2) adding 200 cc/min $H_2$ to the $N_2$ gas flow and holding for 3 hours at 230° F., (3) shut off $N_2$ gas and increasing $H_2$ gas flow to 300 cc/min, (4) heating the reactor temperature to 572° F., holding for 3 hours at 572° F. and then cooled the reactor to 147° F. in 30 cc/min $H_2$ gas flow.

The acetylenic impurities in the same feed used in the Example 10A were removed by selective hydrogenation. The selective hydrogenation was carried out at a constant temperature 142° F. However, the hydrocarbon and hydrogen feed rates were 3.7 ml/min (6.1 WHSV) and 45 scc/min at the reactor pressure of 119 psig, respectively, for the first 73 hours on stream, and then changed to 6.1 ml/min (10.1 WHSV) and 74.2 scc/min at 108 psig, respectively. After 145 hours on stream, the catalyst was washed with benzene (10 ml/min) at 100° C. and 108 psig in 74.2 scc/min $H_2$ flow for 5 hours. The selective hydrogenation was continued at the same condition just before the benzene wash for 24 hours, but benzene (0.6 ml/min) was co-fed to the reactor with the mixed $C_4$ feed. After that, the feed rates were changed to 10 ml/min mixed $C_4$ feed, 1 ml/min benzene, and 90 scc/min $H_2$ for the next 18 hours. And then the feed rates were increased to 15 ml/min mixed $C_4$ feed, 1.5 ml/min benzene, and 112 scc/min $H_2$ at the reactor pressure 95 psig for the next 30 hours. After that, the selective hydrogenation was carried out at a reduced hydrogen rate of 95 scc/min for 24 hours, while keeping other process parameters at the same condition. And then the feed rate was reduced to 10 ml/min mixed $C_4$ feed, 1 ml/min benzene, and 54 scc/min $H_2$ for the next 66 hours, while keeping other process parameters at the same condition.

Figure 8:
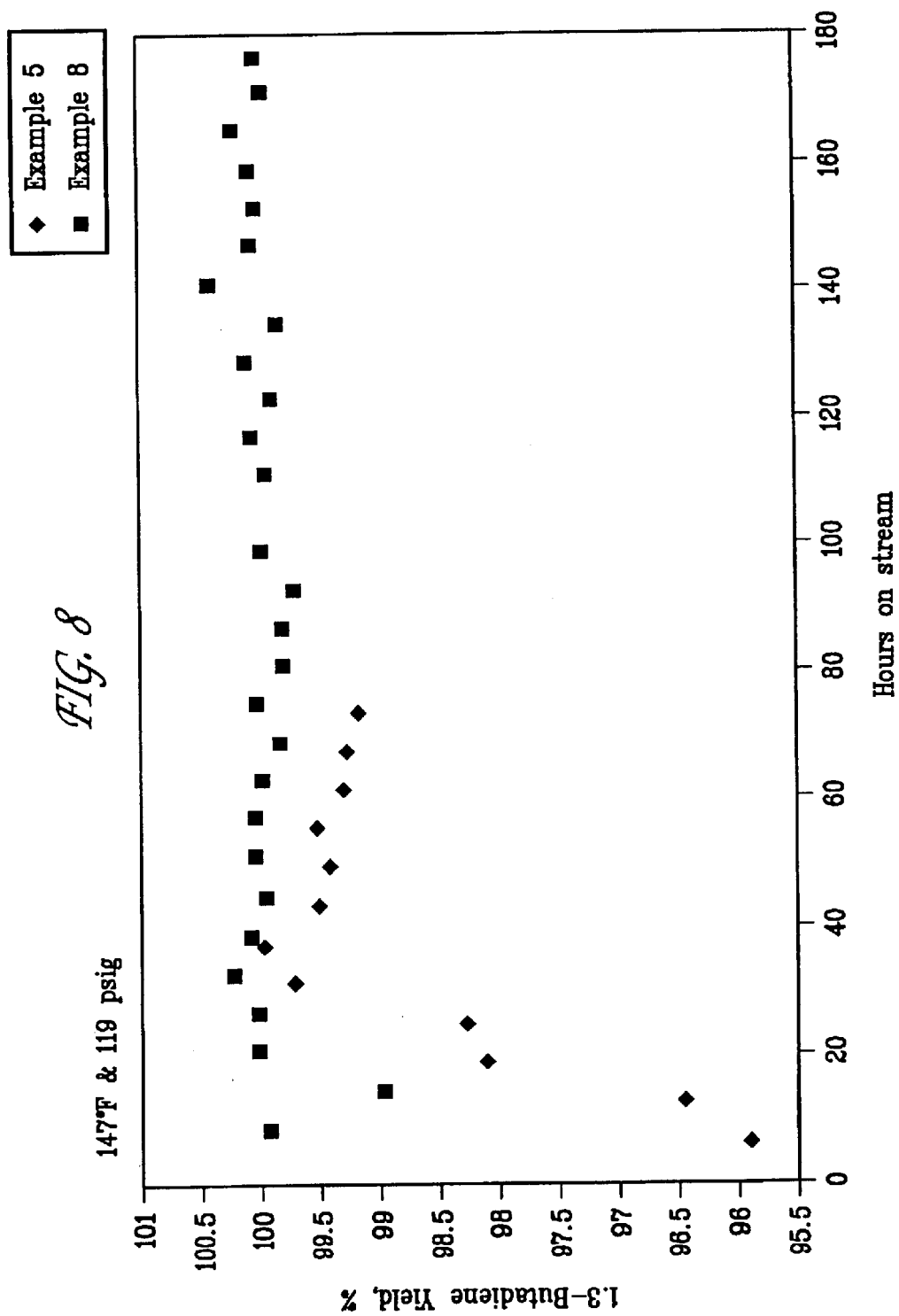
FIG. 8 is a graphic presentation comparing Example 5 (non CD) 1.3-butadiene product and Examples 8 (CD).
Figure 10:
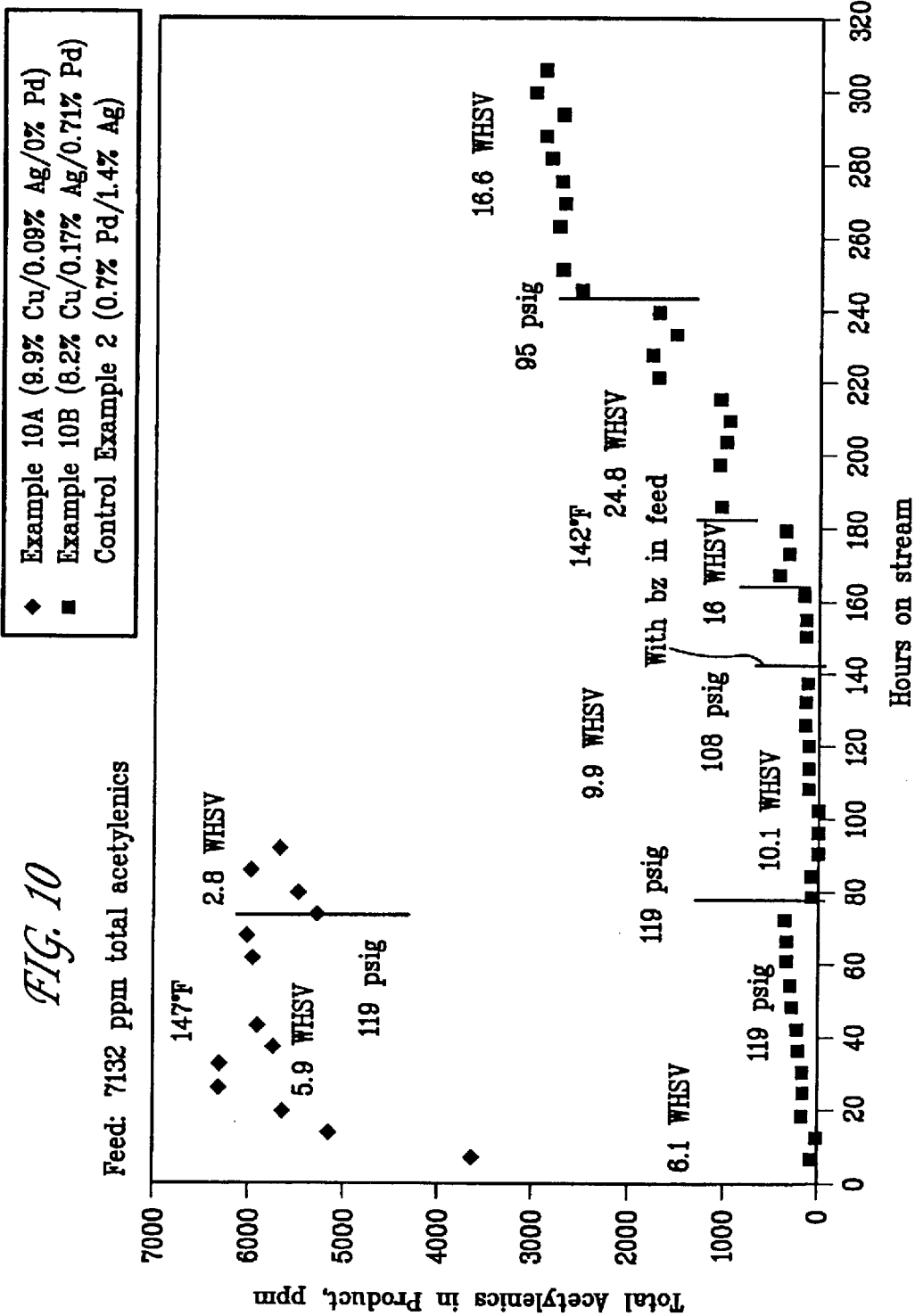
FIG. 10 is a graphic presentation comparing Examples 10A an 10B to show the benefit of Pd promoted Cu.
Figure 11:
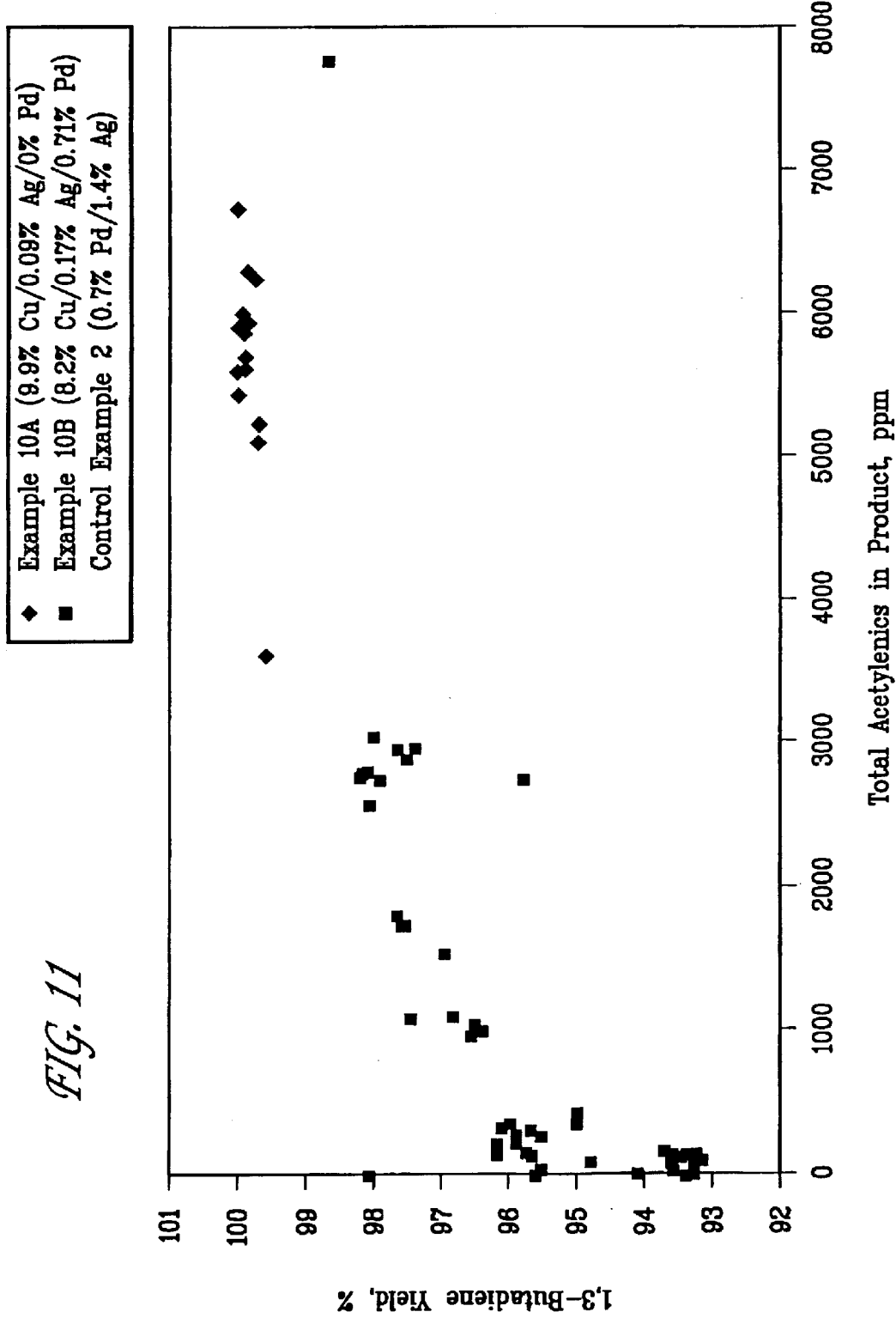
FIG. 11 is a graphic presentation comparing Examples 10A and 10B to show the benefit of Pd promoted Cu on 1,3-butadiene production.

The results of the Examples 10A and 10B are illustrated in FIGS. 10 and 11 along with the Control Example 2. As shown in FIG. 8, the copper catalyst, which was not promoted with palladium, had very low activity in dealing with the high concentration of acetylenic impurities. But when the copper catalyst was promoted with palladium in the technique disclosed in this invention, the catalyst activity was dramatically improved. Surprisingly, the palladium promoted copper catalyst has far superior activity than the commercial Pd selective hydrogenation catalyst. Yet more surprisingly the present palladium promoted catalyst has also a superior 1,3-butadiene yield at the same conversion of the acetylenes over the commercial palladium catalyst despite of its much higher activity. Also the deactivation rate of the palladium promoted catalyst was much better than the commercial Pd catalyst or the unpromoted copper catalyst. This example clearly demonstrates the superior performance of the palladium promoted copper catalyst for the selective hydrogenation of high acetylenic feeds over the palladium catalyst or unpromoted copper catalyst.

EXAMPLE 11

Gamma alumina (obtained from UCI, ⅛ inch extrudates and about 260 $m^2/g$ surface area) was ground to 10–20 mesh granules. According to the supplier of this alumina, the raw material of this alumina is identical to the alumina used in the Control Example 1. But this granular alumina has lower ABD (0.50 g/cc) than the alumina (0.792 g/cc ABD) used in the Control Example 1. A solution of 30 g $Cu(NO_3)_2.6H_2O$, 0.93 g $Ni(NO_3)_2.6H_2O$, 0.047 g $AgNO_3$, 0.396 $Cr(NO_3)_3.9H_2O$ and 0.396 $Co(NO_3)_2.6H_2O$ in 128 ml deionized water was prepared. 70 g of the granular alumina were impregnated with above solution by using a rotary evaporator. After drying the impregnation product in 110° C. in vacuum oven overnight, calcined at 400° C. in a muffle furnace for 3 hours. 18 g of this catalyst was blended with 110 ml 3 mm diameter glass balls and loaded in the same reactor in the Control Example 1. The catalyst was activated by the following procedure; (1) heating the reactor to 230° F. in 100 cc/min $N_2$ gas flow, (2) adding 200 cc/min $H_2$ to the $N_2$ gas flow and then holding for 3 hours at 230° F., (3) shut off $N_2$ gas and increasing $H_2$ gas flow to 300 cc/min, (4) heating the reactor temperature to 662° F. and holding for 3 hours at 662° F. and then cooled the reactor to 147° F. in 30 cc/min $H_2$ gas flow.

The same feed used in the Control Example 1 was selectively hydrogenated to remove acetylene impurities at 119 pig pressure. For the first 29 hours on stream time, the feed hydrocarbon and hydrogen rates were 1.8 cc/min (3.6 WHSV) and 25.7 sc./min, respectively. Then the feed rates were increased to 2.4 cc/min for hydrocarbon (4.9 WHSV) and 34.3 sc./min for hydrogen rate for the next 42 hours on stream. After that, the feed rates was further increased to 3 cc/min for hydrocarbon (6.1 WHSV), but hydrogen feed rate was lowered to 30 sc./min, until the end of the run.

Figure 12:
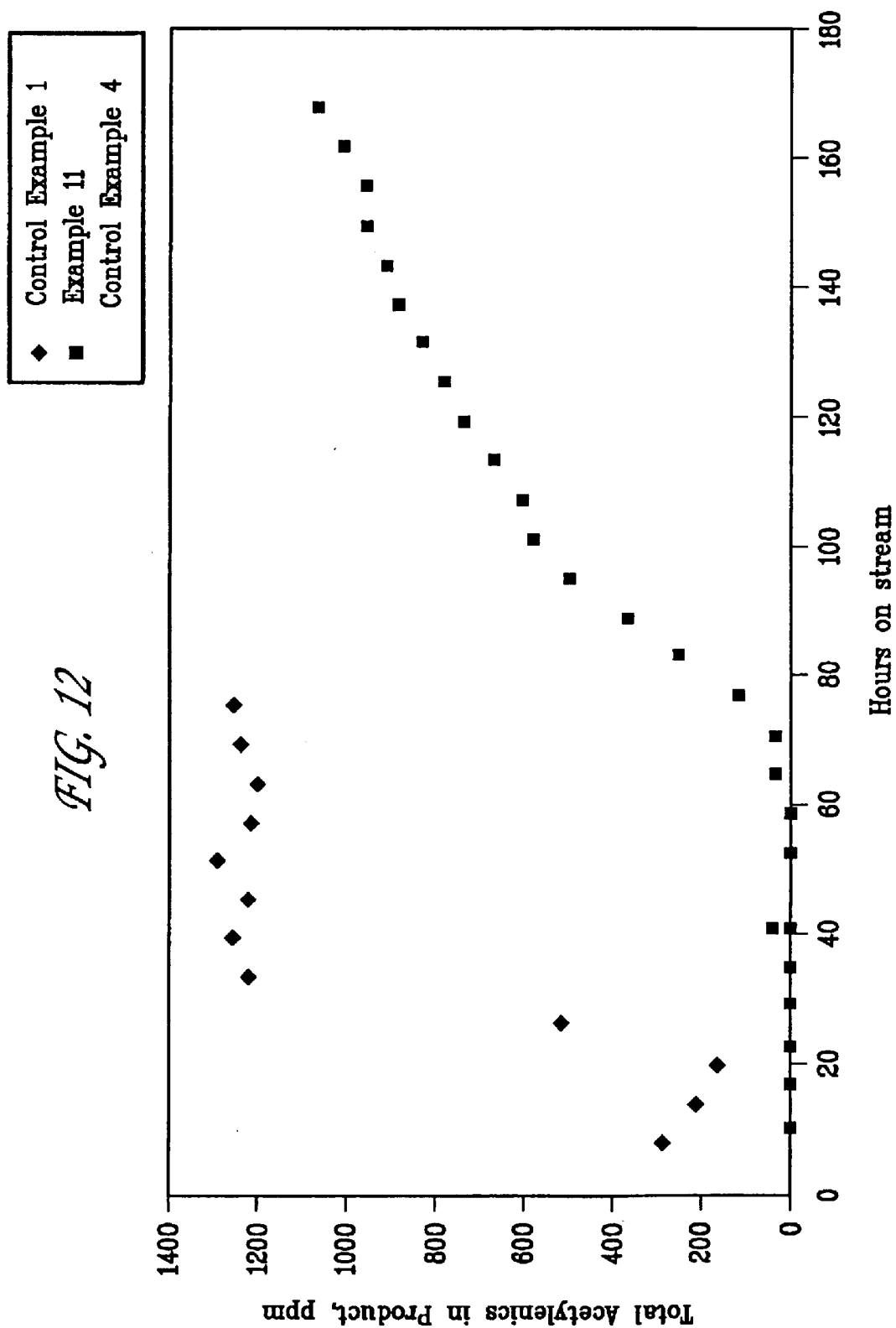
FIG. 12 is a graphic presentation of the benefits of ABD according to the present invention for acetylenes removal comparing Control Examples 1 and 4 and Example 11.
Figure 13:
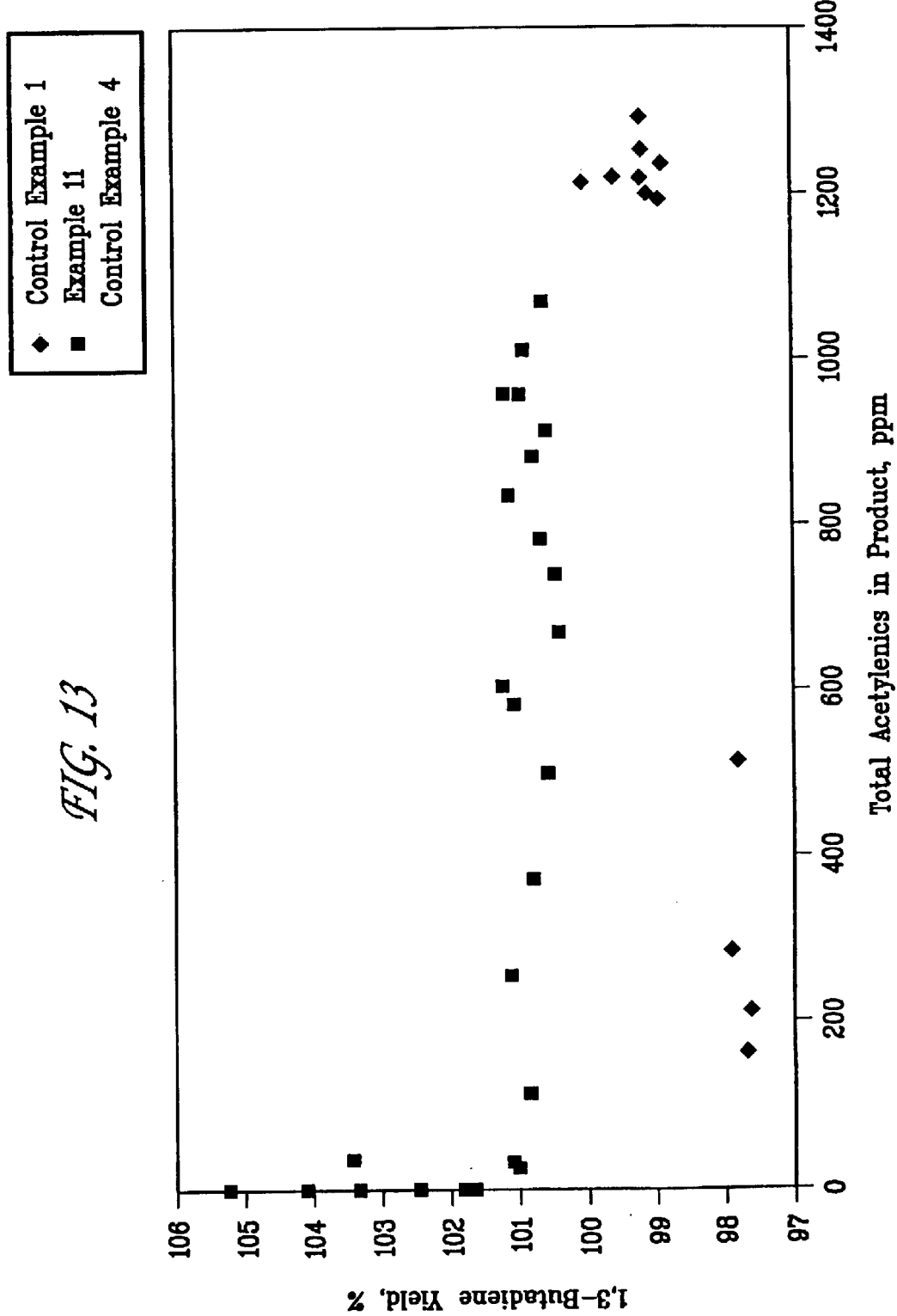
FIG. 13 is a graphic presentation of the benefits of ABD according to the present invention for 1,3-butadiene product comparing Control Examples 1 and 4 and Example 11.

The comparison of the test result of this experiment with those of Control Examples 1 and 4 is illustrated in FIGS. 12 and 13 to demonstrate of the effect of ABD of support aluminas on the catalyst performance. The catalyst prepared using lower ABD alumina, which means higher porosity, in this example outperformed the higher ABD aluminas used in Control Examples 1 and 4. The aluminas in this example and the Control Example 1 were prepared from the same raw materials. But the lower ABD alumina used in this example results in more effective catalyst in removing acetylenic impurities. The catalyst in this example has a better 1,3-butadiene yield than in the Control Example 1. The alumina used to prepare the catalyst in the Control Example 4 has the surface area falling in the preferred range of surface area disclosed in this invention. But the ABD of the alumina in the Control Example 4 is 0.98 g/cc, which is higher than the preferred ABD (<0.65 $g/cm^3$) disclosed in this invention. The effectiveness of the catalyst in the Control Example 4 in removing acetylenic impurities approximately falls in between the Control Example 1 and the Example 11. There is little difference in the yield of the 1,3-Butadiene in the Example 11 and the Control Example 4.

EXAMPLE 12

To demonstrate the superior performance of the palladium promoted copper catalyst for the selective hydrogenation of a feed containing relatively high concentration of acetylenic impurities, this example was carried out.

A copper catalyst promoted with palladium was prepared according to this invention. The alumina used in the Example 5 was calcined at 900° C. for 3 hours in air. A mixed solution was prepared by dissolving 1.866 g $Cu(NO_3)_2 \cdot 2.5H_2O$ in a palladium nitrate solution prepared by diluting 4.61 g 10 wt % $Pd(NO_3)_2$ solution in 10 wt % nitric acid (Aldrich 38,004-0: 10 wt % $Pd(NO_3)_2$) with 6.378 g deionized water. 5.56 g of this mixed solution was sprayed on 30 g of calcined alumina spheres by using an atomizer, while the alumina spheres were rolling around on a flat surface and then the sprayed product was dried at 115° C. in a vacuum oven. The dried product was calcined at 250° C. for 2 hours in air.

18 g of this catalyst was mixed with 110 ml of 3 mm diameter glass balls and loaded in the same reactor used in the Control Example 1. The catalyst was activated in the same manner described in Example 11. The acetylenic compounds in the same feed used in the Control Example 3 were removed by carrying out the selective hydrogenation. The selective hydrogenation was carried out at the constant temperature of 142° F. and 108 psig. The hydrocarbon feed rate was kept at 10 ml/min (20.2 WHSV) until the end of the run. However, variations of hydrogen flow rate in the range of from 44 scc/min to 90 scc/min were made during the run.

Figure 14:
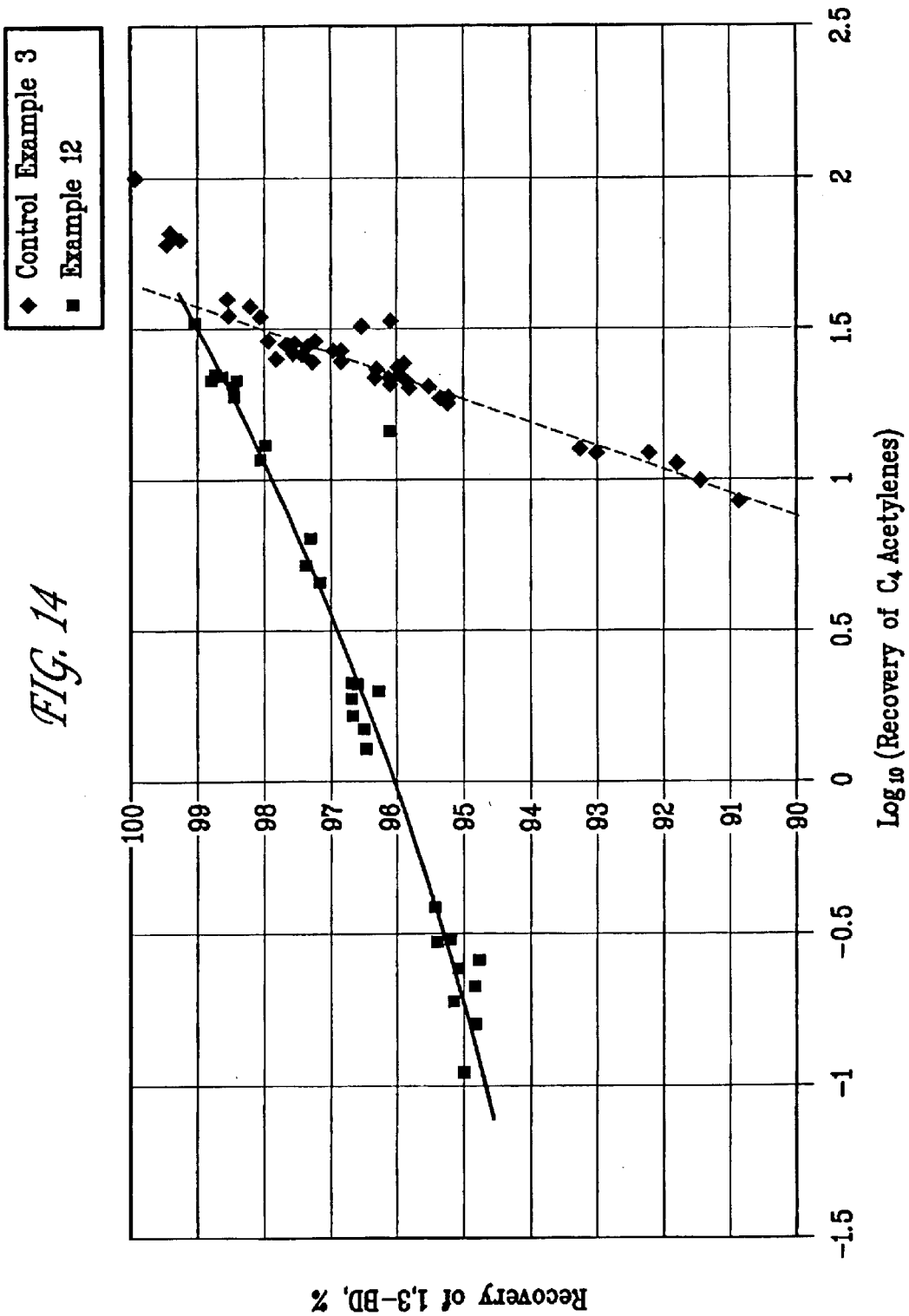
FIG. 14 is a graphic presentation of the benefits of the palladium promoted copper catalyst comparing Example 12 with Control Example 3.
Figure 15:
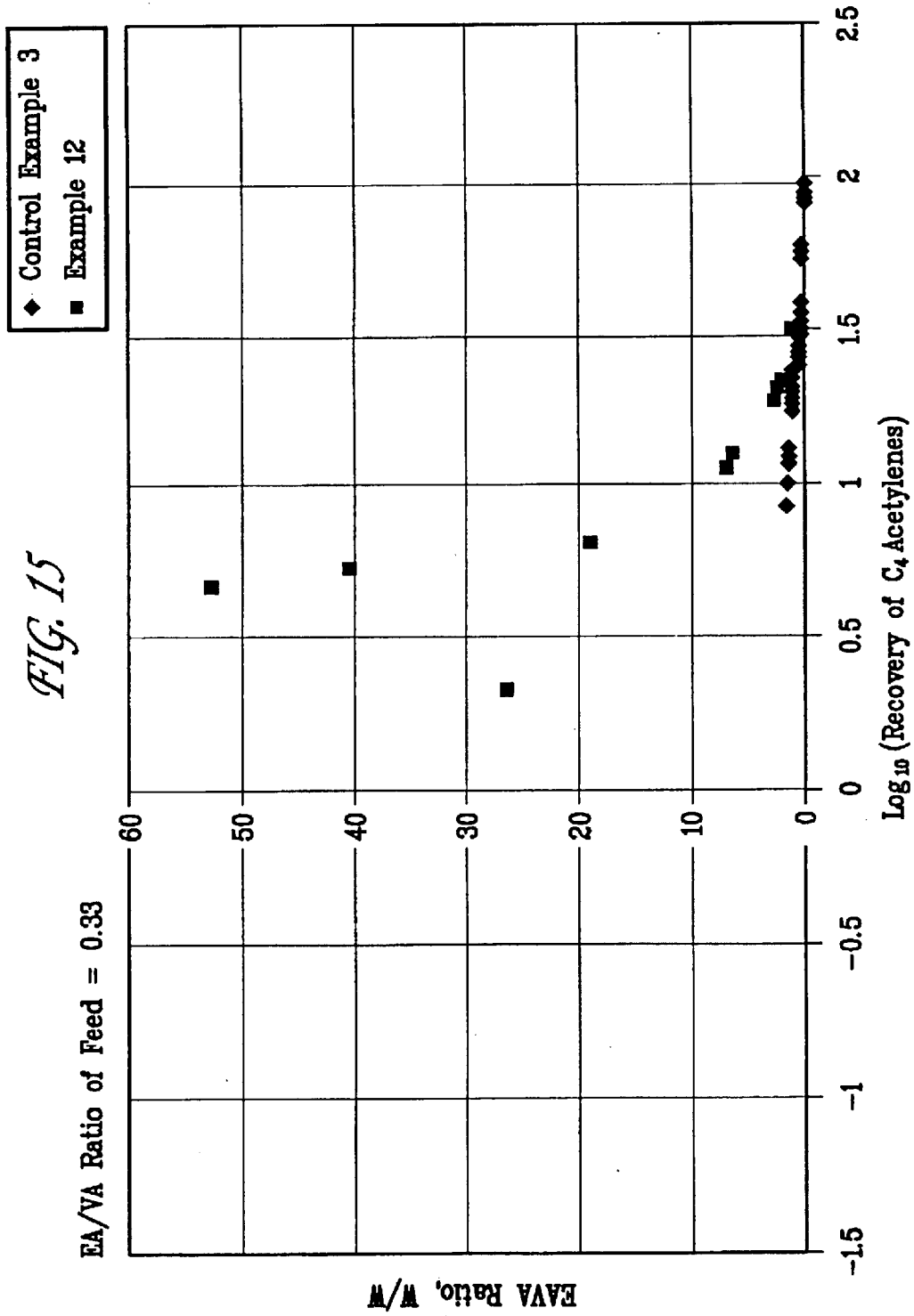
FIG. 15 is a graphic presentation of the chemical fingerprint differentiating the palladium promoted copper catalyst from traditional palladium catalyst by comparing Example 12 with Control Example 3.

The results of this Example 12 and the Control Example 3 are illustrated in FIGS. 14 and 15. The superior catalytic activity of the palladium promoted copper catalyst over the traditional palladium catalyst is clearly demonstrated. Despite a higher feed rate in Example 12 of at least 4 times greater than that of Control Example 3, the palladium promoted copper catalyst is able to produce product containing less than 20 ppm $C_4$ acetylenes with a superior yield (expressed as recovery in FIG. 14) of 1,3-butadiene over the traditional palladium catalyst in Control Example 3. The recovery of C4 acetylenes is defined by 100% vs % conversion of $C_4$ acetylenes; e.g. 0 percent recovery of $C_4$ acetylenes is equivalent to 100% removal of C4 acetylenes and 100% 1,3-butadiene recovery is equivalent to 0% conversion of 1,3-butadiene.

The ratios of ethyl acetylene to vinyl acetylene in the products are illustrated in FIG. 15. The palladium promoted copper catalyst has much higher reactivity toward to vinyl acetylene than the traditional palladium catalyst. The palladium promoted copper catalyst has approximately an order higher activity than the unpromoted copper catalyst. It was unexpected that the palladium promoted copper catalyst has several times higher activity than the traditional Pd catalyst and yet it has a superior selectivity retaining 1,3-butadiene.

The invention claimed is:

1. A process for the selective hydrogenation of acetylenes comprising contacting a feed containing acetylenes in at least partial liquid phase with a catalyst comprising a copper component and a member selected from the group consisting of at least one Group VIII metal component, a Ag component, a Au component and mixtures thereof on an alumina support having apparent bulk density of less than about 0.70 g/cm³, no pores less than about 30 Å diameter, about 90% of pores having pore diameter larger than 100 Å determined by nitrogen porosimetry, BET surface area of 30 to less than about 230 m²/g and total pore volume larger than about 0.65 cc/g under conditions to selectively hydrogenate said acetylenes.

2. The process according to claim 1 wherein a soluble polymer is continuously deposited on said catalyst during said hydrogenation to reduced activity of said catalyst for the selective hydrogenation of acetylenes, and said hydrogenation is intermittently interrupted and a solvent for said soluble polymer is contacted with said catalyst and remove a portion of said polymer and restore a portion of the activity of said catalyst for said selective hydrogenation.

3. The process according to claim 2 wherein said solvent comprises at least one of tetrahydrofuran, furan, 1,4-dioxane, ethers, gamma-butyrolactone, benzene or toluene.

4. A process for the selective hydrogenation of acetylenes comprising contacting a feed containing acetylenes in at least partial liquid phase with a catalyst comprising a copper component, at least one Group VIII metal component and a Zn component deposited on an alumina support having average pore diameter larger than 200 Å, no pores less than about 30 Å diameter, about 90% of pores having pore diameter larger than 100 Å determined by nitrogen porosimetry, BET surface area of 30 to less than about 230 m²/g and total pore volume larger than about 0.65 cc/g under conditions to selectively hydrogenate said acetylenes.

5. The process according to claim 4 wherein a soluble polymer is continuously deposited on said catalyst during said hydrogenation to reduced activity of said catalyst for the selective hydrogenation of acetylenes, and said hydrogenation is intermittently interrupted and a solvent for said soluble polymer is contacted with said catalyst and remove a portion of said polymer and restore a portion of the activity of said catalyst for said selective hydrogenation.

6. The process according to claim 5 wherein said solvent comprises at least one of tetrahydrofuran, furan, 1,4-dioxane, ethers, gamma-butyrolactone, benzene or toluene.

7. The process according to claim 1 wherein the catalyst comprises a member of a Ag component, a Au component or a mixture thereof.

8. The process according to claim 1 wherein the catalyst comprises at least one Group VIII metal component.

9. The process according to claim 1 wherein the catalyst comprises a mixture of at least one Group VIII metal component and a Ag component, a Au component or mixtures thereof component.

10. The process according to claim 1 wherein the catalyst comprises a member of at least one Group VIII metal component or mixture of a Ag component and a Au component.

11. The process according to claim 7, 8, 9 or 10 wherein the Group VIII component comprises Pd.

12. The process according to claim 7, 8, 9 or 10 wherein the catalyst further comprises a Zn component.

13. The process according to claim 1 wherein the catalyst comprises an alumina support having average pore diameter larger than 200 521 .

14. The process according to claim 1 wherein the catalyst comprises an alumina support having an apparent bulk density of less than about 0.70 g/cm³.

15. The process according to claim 4 wherein the catalyst comprises about 0.1 to 25 Wt. % Cu.

16. A process for the selective hydrogenation of acetylenes comprising contacting a feed containing acetylenes in at least partial liquid phase with a catalyst comprising a copper component and a member selected from the group consisting of at least one Group VIII metal component, a Ag component, a Au component and mixtures thereof on an alumina support having average pore diameter larger than 200 Å, no pores less than about 30 Å diameter, about 90% of pores having pore diameter larger than 100 Å determined by nitrogen porosimetry, BET surface area of 30 to less than about 230 m²/g and total pore volume larger than about 0.65 cc/g under conditions to selectively hydrogenate said acetylenes.

17. The process according to claim 16 wherein a soluble polymer is continuously deposited on said catalyst during said hydrogenation to reduced activity of said catalyst for the selective hydrogenation of acetylenes, and said hydrogenation is intermittently interrupted and a solvent for said soluble polymer is contacted with said catalyst and remove a portion of said polymer and restore a portion of the activity of said catalyst for said selective hydrogenation.

18. The process according to claim 16 wherein the catalyst comprises a component of Ag component, a Au component or mixture thereof.

19. The process according to claim 18 wherein the catalyst comprises at least one Group VIII metal component.

20. The process according to claim 19 wherein the catalyst comprises a mixture of a Ag component and a Au component.

21. The process according to claim 16 the catalyst further comprises a Zn component.

22. The process t according to claim 21 wherein the catalyst comprises at least one Group VIII metal component.

23. The process according to claim 4 wherein the catalyst comprises a Ag component, a Au or mixture thereof.

24. The process according to claim 16 wherein said alumina support having an apparent bulk density of less than about 0.70 g/cm$^3$.

25. The process according to claim 1 wherein the catalyst further comprises Ni, Cr, Co or mixtures thereof.

26. The process according to claim 16 wherein the catalyst further comprises Ni, Cr, Co or mixtures thereof.

* * * * *